(12) United States Patent
Medvitz et al.

(10) Patent No.: US 8,666,778 B2
(45) Date of Patent: Mar. 4, 2014

(54) SYSTEMS AND METHODS FOR PROCESSING REQUESTS FOR PHARMACEUTICALS THAT REQUIRE INSURER PREAPPROVAL

(71) Applicant: MedImmune LLC, Gaithersburg, MD (US)

(72) Inventors: Mark Medvitz, Chester County, PA (US); Mike Kumpf, Carroll County, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 13/895,088

(22) Filed: May 15, 2013

(65) Prior Publication Data

US 2014/0006043 A1     Jan. 2, 2014

Related U.S. Application Data

(63) Continuation of application No. 13/312,906, filed on Dec. 6, 2011, now abandoned, which is a continuation of application No. 12/165,477, filed on Jun. 30, 2008, now abandoned.

(60) Provisional application No. 60/937,830, filed on Jun. 29, 2007.

(51) Int. Cl.
*G06Q 50/00* (2012.01)
(52) U.S. Cl.
USPC ........................................ 705/2; 705/3; 705/4
(58) Field of Classification Search
USPC .......................................................... 705/2–4
See application file for complete search history.

(56) References Cited

U.S. PATENT DOCUMENTS

| | | | |
|---|---|---|---|
| 4,491,725 A | 1/1985 | Pritchard | |
| 4,766,542 A | 8/1988 | Pilarczyk | 705/3 |
| 5,845,253 A | 12/1998 | Rensimer et al. | 705/2 |
| 6,584,472 B2 | 6/2003 | Classen | 707/770 |
| 6,670,885 B2 | 12/2003 | Kosaka | |
| 6,985,869 B1 | 1/2006 | Stoll et al. | |
| 6,988,075 B1 | 1/2006 | Hacker | |
| 7,072,840 B1 | 7/2006 | Mayaud | |
| 7,286,996 B1 | 10/2007 | Fiedotin et al. | |

(Continued)

OTHER PUBLICATIONS

Agency for Healthcare Research and Quality, Apr. 2007, "Findings From the Evaluation of E-Prescribing Pilot Sites," Publication No. 07-0047-EF, pp. i-x and 1-117.

(Continued)

*Primary Examiner* — Sind Phongsvirajati
(74) *Attorney, Agent, or Firm* — Mueting, Raasch & Gebhardt, P.A.

(57) ABSTRACT

Systems, methods, and apparatus for managing patients in need of a predetermined pharmaceutical that requires preauthorization based upon patient clinical data are provided. Prescription information is obtained for each respective patient. Such information includes an identity of the patients and amounts of the pharmaceutical that has been prescribed to the patients. Further, clinical information associated with each patient is received. The clinical information one or more determinants that each contributes to providing a basis for authorizing or denying patient coverage for the pharmaceutical. At least one determinant in the one or more determinants is not a standardized code. Coverage for a patient for the predetermined pharmaceutical is requested by transmitting the prescription and clinical information to a specialty pharmaceutical distributor at a remote location. A grant or denial of coverage for the patient is then received from the remote location and stored in an electronic record associated with the patient.

20 Claims, 28 Drawing Sheets

(56) References Cited

U.S. PATENT DOCUMENTS

| | | | |
|---|---|---|---|
| 7,321,861 B1 | 1/2008 | Oon | |
| 7,909,763 B2 | 3/2011 | Abel | 600/300 |
| 2003/0074225 A1 | 4/2003 | Borsand et al. | 705/3 |
| 2003/0149599 A1 | 8/2003 | Goodall et al. | 705/2 |
| 2005/0278196 A1 | 12/2005 | Potarazu et al. | 705/2 |
| 2006/0161461 A1 | 7/2006 | Trani et al. | 705/4 |
| 2006/0229551 A1 | 10/2006 | Martinez et al. | |
| 2006/0229910 A1 | 10/2006 | Longman et al. | |
| 2006/0235280 A1 | 10/2006 | Vonk et al. | |
| 2006/0235726 A1 | 10/2006 | Paraison et al. | |
| 2006/0259330 A1 | 11/2006 | Schranz | |
| 2006/0277075 A1 | 12/2006 | Salwan | |
| 2007/0021988 A1 | 1/2007 | Dang | 705/4 |
| 2007/0067186 A1 | 3/2007 | Brenner | |
| 2007/0093935 A1 | 4/2007 | Fu | |
| 2007/0143141 A1 | 6/2007 | Villasenor | |
| 2007/0150092 A1 | 6/2007 | Ohmura | |
| 2007/0168223 A1 | 7/2007 | Fors | |
| 2007/0219827 A1 | 9/2007 | Green | |
| 2007/0293982 A1 | 12/2007 | Rosenblum | |
| 2008/0015897 A1 | 1/2008 | Moradi | |
| 2008/0017722 A1 | 1/2008 | Snyder | |
| 2008/0021739 A1 | 1/2008 | Brock | |
| 2008/0040602 A1 | 2/2008 | Williams | |
| 2008/0046294 A1 | 2/2008 | Fiedotin | |
| 2008/0091468 A1 | 4/2008 | Heidenreich | |
| 2008/0103626 A1 | 5/2008 | Frankel | |
| 2008/0120207 A1 | 5/2008 | Strickland | |
| 2008/0133274 A1 | 6/2008 | Warner | |
| 2008/0133511 A1 | 6/2008 | Schoenberg | |
| 2008/0140250 A1 | 6/2008 | Dave | |
| 2008/0154646 A1 | 6/2008 | Barrett | |
| 2009/0024412 A1 | 1/2009 | Medvitz et al. | |
| 2012/0203570 A1 | 8/2012 | Medvitz et al. | |

OTHER PUBLICATIONS

Anonymous, Winter 2007, "Medication Safety: IOM Report Calls for E-Prescribing, More Engaged Consumers," Hospitals & Health Networks, 6, p. 56.
Barich et al., 2007, "Centers for Medicare and Medicaid Services Special Study Pilot Testing of Electronic Prescribing Standards," Grant No. SS-OH-01, Final Report, 1-118.
Bell et al,, 2007, "Pilot Testing of Electronic Prescribing Standards," Agency for Healthcare Research and Quality Grant No. 1U18HS016391-01, 1-20.
Brin, 2007, "E-Prescribing May Grow As Industry Makes a Push," Wall Street Journal (Eastern Edition), B.5A.
Brushwood, 2003, "Maxintizing the value of electronic prescription monitoring programs,", The Journal of Law, Medicine & Ethics 31, 41, 8-9, 42-54, 4.
City's Public Hospitals Leading Trend in Electronic Prescription Technology to Reduce Drug Errors, Jul. 27, 2006, U.S. Fed. News Service.
Deadline Extended to Accept E-Prescribing Grant Applications, Dec. 1, 2006, U.S. Fed News Service.
Electronic Healthcare Network Accreditation Commission, May 5, 2007, "First EHNAC E-Prescribing Network Accreditation," Obesity, Fitness & Wellness Week, 593.
Electronic Prescriptions; Program to deliver electronic prescribing to Tennessee physicians, Jan. 9, 2005, Nursing Home & Elder Business Week, 39.
Finkelstein, 2006, "E-Prescribing First Step to Improved Safety," Journal of the National Cancer Institute 98, 1763-1765.
Frederick, 2007, "SureScripts boosts e-prescribing links with purchase of MedAvant's network," Drug Store News 29, 65.
Gooch, 2006, "Providers and payers work to ease into e-prescribing" Managed Healthcare Executive 16, 52, 54.
Havenstein, 2007, "Wellpoint Learns From Earlier E-prescribing Failure," Computerworld 41, 6.
HHS Issues Report to Congress on E-Prescribing Electronic Prescribing to Cut Errors, Costs, Apr. 17, 2007, U.S. Fed News Service.
Information Technology; IT company, electronic prescription data provider reach services agreement, Nov. 28, 2004; Medical Devices & Surgical Technology Week, 204.
InstantDx, LLC, Jun. 23, 2007, InstantDx Celebrates TEPR E-Prescribing Award Obesity, Obesity, Fitness & Wellness Week, 818.
Kaufman, 2007, "E-prescribing offers a neat and safe alternative to pad and pen," Formulary 42, 250.
Leavitt, 2007, "Pilot Testing of Initial Electronic Prescribing Standards—Cooperative Agreements Required Under Section 186D-(4)(e) of the Social Security Act as Amended by the Medicare Prescription Drug, Improvement, and Modernization Action (MMA) of 2003," 1-35.
Long Term Care e-Prescribing Standards Pilot Study, Final Report,Jun. 19, 2007, 1-48.
Medicare and Medicaid, May 6, 2007, "RxHub ePrescribing Standards Recommended for Use in Medicare Part D," Medical Letter on the CDC & FDA, 50.
Minnesota State Employee Health Plan to Use E-Prescribing, Jun. 6, 2007, U.S. Fed News Service.
Murray, 2007, "Free e-prescribing software for all," Medical Economics 84, 14.
Research and Markets Ltd., May 12, 2007, "How ePrestribing is Influencing the Modern Healthcare Market," Obesity, Fitness & Wellness Week, 1056.
Robeznieks, 2007, "E-prescribing disconnect," Modern Healthcare 37, 12-13.
Rothschild et al., 2007, "Electronic Prescribing Using a Community Utility: The ePrescribing Gateway," Final Report, Agency for Healthcare Research and Quality, Centers for Medicaid and Medicare Services, Notice of Grant Award 1U18HS016377-01, 1-20.
RxHub LLC, 2007, "RxHub Hosts Workgroup Focused on MMA ePrescribing Pilots, Medication Claims History Findings, and Transaction Standards Enhancements," Biotech Week, 991.
Scalise, 2007, "The Case for e-prescribing," Hospitals & Health Networks, 81, pp. 45-51.
Security Biometrics, Inc.; Electronic prescriptions application geared to reduce prescription errors, Mar. 24, 2004, Biotech Week, p. 443.
Sylvain 2007, "U.S. MDs on the fence about e-prescribing," Medical Port 43, 79.
Wollenberg, 2007, "E-prescribing: Not out of the woods yet," Medical Economics 84, 17.
Office Action issued Oct. 27, 2010, in U.S. Appl. No. 12/165,477, filed Jun. 30, 2008.
Office Action issued Jul. 7, 2011, in U.S. Appl. No. 12/165,477, filed Jun. 30, 2008.
Office Action issued Nov. 8, 2012, in U.S. Appl. No. 13/312,906, filed Dec. 6, 2011.
Office Action issued Feb. 19, 2013, in U.S. Appl. No. 13/312,906, filed Dec. 6, 2011.

Synagis® (palivizumab) Statement of Medical Necessity

Referral #:      SPD:

| Aetna Specialty Ex | Orlando | FL | 866-782-2778 | 866-329-2779 |
|---|---|---|---|---|

PATIENT INFORMATION

Last Name: Forman      First Name: Fred
184 Mendocino Drive, Alexandria      Virginia 23114
DOB: 01/03/2007 Sex: Unknown      Social Security Number: 223-08-9999
Patient Parent/Guardian: Alan Forman
Day Phone: (555)-55-5555

INSURANCE INFORMATION

Primary Insurance
Primary Insurance: ADVANTAGE Health Solutions, Inc. Commercial
Primary Cardholder Name:      Alan Forman
Primary Cardholder Social Security
Number:      223-08-9999
Primary Policy Number:      324242-234243234
Primary Insurance Telephone:      (555)252-2323
Primary Employer:      Aetna
Primary Group Number:      555232
Drug Benefit: PBM      32423423
Insurance:      Aetna Pharmacy Management (APM)
Specialty Pharmacy Provider

| Aetna Specialty Rx | Orlando | FL | 866-782-2779 | 866-329-2779 |
|---|---|---|---|---|

PHYSICIAN INFORMATION

Prescriber: Roberts Henry E.      Practice Name: Metro Pediatrics
Shipping Address: Address 23 Bozeman
Montana
11233
Phone:      (555)888-8888      Dea Number:    Dea Num
License Number: Li Num      UPIN Number: UPIN Num
Office contact: Brett Lovejoy
National Provider Identifier (NPI): 2520
Medical Provider Number: 2233

CLINICAL INFORMATION

Primary Diagnosis:

Fig. 13B

Patient's Gestational Age (GA): 23 weeks
<= 24 weeks GA (ICD9: 765.21 - 765.22)
Current weight: 9 Lb   Weight recorded: 6/5/2007
Congenital heart disease: (745.0-747.9)
Chronic Respiratory conditions of Fetus and Newborn: (770.0-770.9)
Congenital anomalies of respiratory system: (748)
Medical Criteria Diagnosis 1
Diagnosis of chronic pulmonary disease (CLD/BPD) and less than 24 months of age: Yes

| | | |
|---|---|---|
| The patient receives Oxygen | Last date Oxygen received: | 3/15/2007 |
| The patient receives Corticosteroids | Last date Corticosteroids received: | 5/14/2007 |
| The patient receives Diuretics | Last date Diuretics received: | 6/7/2007 |
| The patient receives Bronchodilator | Last date Bronchodilator received: | 5/7/2007 |

Diagnosis 2
Diagnosis of hemodynamically significant congenital heart disease and less than 24 months of age: Yes
Patient has Diagnosis of moderate to severe pulmonary hypertension: Yes
Cyanotic: Yes Symagis NICU History
Did the patient spend time i the NICU: Yes
Was RSV prophylaxis recommended by the NICU/HOSPITAL physicians for the patient: Yes Rx
Symagis Liquid Solution Quantity: QS Sig: Inject 15mg/kg IM every month (28-30 days) Refill: 6 times
Epinephrine: 1:1000 amps #1 Sig: Inject 0.01 mg/kg as directed Refill: PRN
Known allergies: none I acknowledge that the coding used above is/are the appropriate code(s) for this patient and accurately reflects this patient's medical history.

Provider: henry E. Roberts          Signature: _____

| Patient Roster | Patient | User | Practice Profile | Package Insert | Important Safety Info. |

— 2150
— 70

User Details

| User Name * | medvitzm | MRN * | 123 | User Type * | Doctor | ☑ Active |
| Last Name * | Medvitz | First Name * | Mark | License number | 123 | Title |
| Department | ☒ | Default Role * | Doctor | Default specialty * | MedImmune | |

✚ Address
✚ Associations
✚ eForm...

2210

Henry E. Roberts M.D.    Login time 06/10/2007 10:50 PM    Powered by ◆CliniWorks    💾 Save    🗑 Delete    ✖ Close    Logout ☒

Fig. 23

VisionIT - Windows Internet Explorer https://www.visionemr.com/MI/Main.aspx

VISION ContecVision SYNAGIS PALIVIZUMAB                                    MedImmune

Select patient

| Patient Roster | Patient | Practice Profile | Package Insert | Important Safety Info. |

| | Referral # | Patient Name | Location | Provider | Insurance | SPD | Status time |
|---|---|---|---|---|---|---|---|
| | 070000207 | Ana James | Test Practice | | AMERIGROUP Virginia AMERIGROUP Virginia | | 11:44 AM 05/22/2007 |
| | 070000210 | Bubba Medvitz | Test Practice | John D Smith | Aetna | Alegent Health | 4:41 PM 05/23/2007 |
| | 070000211 | name last | Test Practice | A Dr A | Atlantis Health Plan (AHP) | Aetna Specialty Rx | 4:23 PM 05/24/2007 |
| | 070000212 | a Aladin | Test Practice | John D Smith | AMERIGROUP Maryland, Inc. | Accredo | 4:56 PM 05/24/2007 |
| | 070000213 | b Ali | Test Practice | John D Smith | PacifiCare of Arizona, Inc. | Caremark Inc | 4:58 PM 05/24/2007 |
| | 070000214 | c Ali | Test Practice | Henry E. Roberts | Blue Cross and Blue Shield of Michigan | | 5:01 PM 05/24/2007 |
| | 070000215 | name last | Test Practice | | | Caremark Inc | 1:05 PM 05/27/2007 |
| | 070000216 | aa aa | Test Practice | Henry E. Roberts | | | 1:07 PM 05/27/2007 |
| | 070000217 | patient last | Test Practice | Henry E. Roberts | | | 2:05 PM 05/28/2007 |
| | 070000218 | cc cc | Test Practice | Henry E. Roberts | | | 2:10 PM 05/28/2007 |

Results number 29 Found (100 Last records will be displayed)

Date [All Dates ▼] Provider [ ] First Name [ ]
Status [All States ▼] Location [ ] Last Name [ ]

Search    Clear

Henry E. Roberts M.D.    Login time 06/08/2007 03:07 PM

Fig. 26

SYSTEMS AND METHODS FOR PROCESSING REQUESTS FOR PHARMACEUTICALS THAT REQUIRE INSURER PREAPPROVAL

CROSS REFERENCE TO RELATED APPLICATIONS

This application is a continuation under 35 U.S.C. §120 of U.S. patent application Ser. No. 13/312,906 entitled "Systems and Methods for Processing Requests for Pharmaceuticals that Require Insurer Preapproval," filed Dec. 6, 2011, which is a continuation of U.S. patent application Ser. No. 12/165,477 entitled "Systems and Methods for Processing Requests for Pharmaceuticals that Require Insurer Preapproval," filed Jun. 30, 2008, abandoned, which claims priority to U.S. Provisional Patent Application No. 60/937,830 entitled "Systems and Methods for Processing Requests for Pharmaceuticals that Require Insurer Preapproval," filed Jun. 29, 2007, the entire contents of each of which are hereby incorporated by reference herein.

FIELD OF THE INVENTION

The present invention relates to systems and methods for processing a request for a prescription for a predetermined pharmaceutical that requires preauthorization based upon clinical data of a patient.

BACKGROUND

There exists a wide range of specialty pharmaceuticals such as SYNAGIS® (MedImmune, Gaithersburg, Md.). In the case of SYNAGIS®, the specialty pharmaceutical is a unique injectable biologic. SYNAGIS® is one of the very few specialty pharmaceuticals that are used in all treatment settings: hospitals, doctors, home care companies. SYNAGIS® has to be administered by a health care professional. Consequently, it is not a self-administrable pharmaceutical. It is used on premature infants primarily and it is non-chronic. The premature infants who get the specialty pharmaceutical usually do so during the cold and flu season. Patients are treated roughly from October to March, depending on where they are in the United States and the terms and conditions of their payer policy. Once a patient has been subjected to a SYNAGIS® treatment regimen, they no longer require the specialty pharmaceutical in subsequent years. SYNAGIS® prevents a severe viral infection that in many cases can hospitalize a premature baby and in a very small number of cases, actually result in death. SYNAGIS® is a relatively high-cost specialty pharmaceutical in the pediatrics space. Assuming that a subject gets approximately five doses of SYNAGIS® in a treatment regimen, the cost for administration can be thousands of dollars.

The problem in the art that specialty pharmaceuticals such as SYNAGIS® presents are the widely varying conditions and circumstances under which insurance covers each patient for such drugs. In many instances, an insurance plan may not cover certain products. And, while in most instances insurance plans do cover specialty pharmaceutical such as SYNAGIS®, the conditions under which each such insurance plan covers such drugs widely varies. For instance, the patient selection criteria vary from insurance payer by insurance payer. Additionally, in the case of SYNAGIS®, the season length varies by region of the country and by payer policy. Furthermore, in the case of SYNAGIS®, because it is a pediatric specialty pharmaceutical, each and every year pediatricians must identify and qualify an entirely new patient pool. Another complication associated with drugs, such as SYNAGIS®, is that specialty pharmacy distributors supply them. In the United States, there are several hundred such distributors that distribute specialty pharmaceutical such as SYNAGIS®.

A specialty pharmacy distributor has functionality equivalent to a mail order center, only for high-cost biologics. To order a specialty pharmaceutical for a patient, a physician has to complete a form and send it the specialty pharmacy. The form is typically one sheet long and includes information pertaining to identification of the patient, the patient's insurance, and the patient's clinical circumstances. The form as a practical matter serves two functions. First, it serves to provide the specialty pharmacy with information to get the product preauthorized by the payer, and second, assuming the patient qualifies, it serves as a prescription by which the pharmacy can then legally dispense the drug. Presently, over the course of the specialty pharmaceutical's life, all this is done on paper and by Fax. This conventional practice, while functional, is unsatisfactory. Often, the paper forms are incomplete or illegible, which means that the specialty pharmacy that receives the form has to contact the physician's office for additional clinical information, additional demographic or insurance information, or quite literally to understand what the doctor wrote on the form. Conversely, physicians are faced with the problems of (i) identifying a suitable specialty pharmacy that sells the specialty pharmaceutical to send the forms to and (ii) determining what information is required by such a specialty pharmacy. As indicated above, given the widely varied requirements of the insurance plans that cover the products such as SYNAGIS®, coupled with the varied rules and procedures of the numerous specialty pharmacists that sell such products, there is no uniformity in the information required by specialty pharmacies.

Moreover, adding to the complexity in ordering specialty pharmaceuticals, because of their relatively high costs and the widely varying conditions under which insurance companies authorize their use, physician requests for such drugs are scrutinized and, in some instances, denied. When a request is denied, a physician may appeal the denial. As in the case of ordering the specialty pharmaceutical in the first place, the appeal process varies from insurance company to insurance company.

In the art, there exists e-prescribing software and hardware that electronically transfers prescription information. E-prescribing is useful in situations where a doctor wishes to send a request electronically to a pharmacy without having to provide a written script to the patient. This is advantageous for several reasons, including the elimination of problems that arise from handwriting legibility, the convenience to the pharmacist, and to the patient. For instance, rather than hand delivery a script to the pharmacists and then waiting for up to an hour for the prescription to be filled, the prescription can already be filled when the patient arrives at the pharmacists. The United States government has supported e-prescribing initiatives and it has met an enthusiastic response in the medical community. However, e-prescribing is not in widespread use to date. Moreover, with respect to specialty pharmaceuticals, known e-prescribing systems do not have a mechanism for providing additional clinical information with the request for a prescription. Thus, known e-prescribing systems fail to provide any kind of information for drugs that might require prior authorization from insurance provider. As a consequence, e-prescribing is limited to common pharmaceuticals that don't require prior clinical-based review by the insurance provider prior to authorization. Additionally, there are systems used by vendors that will store and convey insurance information or patient demographics. However, such systems do not have means for attaching a prescription.

Given the above background, what is needed in the art are improved systems and methods for ordering specialty pharmaceuticals.

SUMMARY

One aspect provides a method for processing a request for a prescription for a predetermined pharmaceutical that requires preauthorization based upon clinical data of a patient. In the method prescription information is obtained for the patient. The prescription information comprises an identity of the patient and an amount of the predetermined pharmaceutical. Further, clinical information associated with the patient is received. The clinical information comprises one or more determinants, where each such determinant contributes to a basis for authorizing or denying coverage to the patient for the predetermined pharmaceutical. At least one of these determinants is not a standardized code. In the method a determination as to whether to grant coverage to the patient for the predetermined pharmaceutical based upon the prescription information and the clinical information is made. Further, the coverage decision is communicated to a user interface device, a monitor, a computer-readable storage medium, a computer-readable memory, or a local or remote computer system, or the coverage decision is displayed. A remote computer system is a computer system that is accessed over a network connection. The network connection can be supported by a physical cable or a wireless communication. An example of a network connection is the Internet. A remote computer that is being accessed is typically in a different building or even a different state than the person or process that is accessing the remote computer, communicating information to the remote computer, or retrieving information from the remote computer.

In some embodiments, the clinical information is a gestational age of the patient, a weight of the patient, a categorical indication as to whether the patient has congenital heart disease, a categorical indication as to whether the patient has chronic respiratory disease arising in the perinatal period, a categorical indication as to whether the patient has a chronic pulmonary disease, and/or a categorical indication as to whether the patient has a congenital anomaly of the respiratory system. In some embodiments the clinical information comprises a categorical indication as to whether the patient has congenital heart disease and, when the patient has congenital heart disease, the group of determinants further comprises a categorical indication as to whether the patient has moderate or severe pulmonary hypertension, an identity of a medication that is being given to the patient for the congenital heart disease, and a date when the medication for the congenital heart disease was administered to the patient. In some embodiments, the clinical information comprises a categorical indication as to whether the patient has a chronic pulmonary disease and, when the patient has the chronic pulmonary disease, the group of determinants further comprises a categorical indication as to whether the patient receives supplemental oxygen, a categorical indication as to whether the patient receives a corticosteroid, a categorical indication as to whether the patient receives a diuretic, and/or a categorical indication as to whether the patient receives a bronchodilators.

In some embodiments, an age of the patient is determined from the clinical information or the prescription information and coverage to the patient for the predetermined pharmaceutical is denied when the patient is more than two years old. In some embodiments, the clinical information comprises at least two determinants, at least three determinants, at least four determinants, or at least five determinants from the group of determinants consisting of a gestational age of the patient, a weight of the patient, a categorical indication as to whether the patient has congenital heart disease, a categorical indication as to whether the patient has chronic respiratory disease arising in the perinatal period, a categorical indication as to whether the patient has a chronic pulmonary disease, and a categorical indication as to whether the patient has a congenital anomaly of the respiratory system.

In some embodiments, the clinical information comprises one or more risk factors, two or more risk factors, three or more risk factors, four or more risk factors, or five or more risk factors selected from the group consisting of a categorical indication as to whether the patient has a school age sibling, a categorical indication as to whether the patient has been subjected to an air pollutant, a categorical indication as to whether the patient attends day care, a categorical indication as to whether the patient has severe neuromuscular disease, a categorical indication as to whether the patient is subject to crowded living conditions, a categorical indication as to whether the patient had a birth weight of less than 2500 grams, a categorical indication as to whether the patient was part of a multiple birth, a categorical indication as to whether there is a history of asthma in the patient's family, a categorical indication as to whether the patient suffers from a congenital abnormality or airway, and/or a categorical indication as to whether the patient has been exposed to tobacco smoke.

In some embodiments, the prescription information and the clinical information for the patient is received from a remote computer in a packet-based form over a wide area network or Internet. In some embodiments, the prescription information and the clinical information for the patient is received in a secure manner over the wide area network or Internet. In some embodiments, the prescription information and the clinical information for the patient are received using the Hypertext Transport Protocol over a secure socket layer.

In some embodiments the determining step and the communication step of the methods are each done without human intervention. In some embodiments, the prescription information for the patient further includes one or more, two or more, three or more, four or more, five or more, six or more, or seven or more insurance information elements selected from the group consisting of identification of the primary insurer for the patient, a primary cardholder name, a primary cardholder social security number, a primary policy number, a primary insurer telephone number, a primary employer, a primary group number, an identification of a secondary insurer for the patient, a secondary cardholder name, a secondary cardholder social security number, a secondary policy number, a secondary insurer telephone number, a secondary employer, and a secondary group number.

Another aspect provides a computer-readable medium storing a computer program product, executable by a computer, to process a request for a prescription for a predetermined pharmaceutical that requires preauthorization based upon clinical data of a patient. The computer program comprises instructions for obtaining prescription information for the patient, wherein the prescription information comprises an identity of the patient and an amount of the predetermined pharmaceutical. The computer program product further comprises instructions for receiving clinical information associated with the patient, where the clinical information comprises one or more determinants and where each determinant in the one or more determinants contributes to a basis for authorizing or denying coverage to the patient for the predetermined pharmaceutical. In some embodiments, at least one, at least two, at least three, at least four, or at least five of the determinants in the one or more determinants is not a standardized code. The computer program product further comprises instructions for determining whether to grant coverage to the patient for the predetermined pharmaceutical based upon the prescription information and the clinical information. The computer program product further comprises instructions for communicating the coverage decision to a user interface device, a monitor, a computer-readable storage medium, a computer-readable memory, or a local or remote computer system, or displaying the coverage decision.

Still another aspect comprises an apparatus for processing a request for a prescription for a predetermined pharmaceutical that requires preauthorization based upon clinical data of a patient. The apparatus comprises a processor and a memory, coupled to the processor. The memory stores a module comprising instructions for obtaining prescription information for the patient, where the prescription information comprises an identity of the patient and an amount of the predetermined pharmaceutical. The module further comprises instructions for receiving clinical information associated with the patient, where the clinical information comprises one or more determinants and where each determinant in the one or more determinants contributes to a basis for authorizing or denying coverage to the patient for the predetermined pharmaceutical, and where at least one determinant in the one or more determinants is not a standardized code. The module further comprises instructions for determining whether to grant coverage to the patient for the predetermined pharmaceutical based upon the prescription information and the clinical information. The module further comprises instructions for communicating the coverage decision to a user interface device, a monitor, a computer-readable storage medium, a computer-readable memory, or a local or remote computer system, or displaying the coverage decision.

Yet another aspect provides a method for managing a plurality of patients that are each in need of a predetermined pharmaceutical that requires preauthorization based upon patient clinical data. In the method prescription information for each respective patient in the plurality of patients is received. The prescription information comprises an identity of the respective patient and an amount of the predetermined pharmaceutical that has been prescribed to the patient. In the method, clinical information associated with each respective patient in the plurality of patients is also received. The clinical information for each respective patient comprises one or more determinants and each determinant in the one or more determinants contributes to a basis for authorizing or denying coverage to the respective patient for the predetermined pharmaceutical. At least one, at least two, at least three, at least four, or at least five determinants in the one or more determinants is not a standardized code. In the methods, coverage for a patient in the plurality of patients is requested for the predetermined pharmaceutical by transmitting the prescription information and the clinical information to a specialty pharmaceutical distributor at a remote location by electronic means. Further, in the method, a grant or denial of coverage for a patient in the plurality of patients is received for the predetermined pharmaceutical. The grant or denial of coverage for the patient is stored in a record associated with the patient.

In some embodiments, the clinical information for a patient in the plurality of patients comprises at least one, at least two, at least three, at least four, at least five, or at least six determinants from the group of determinants consisting of a gestational age of the patient, a weight of the patient, a categorical indication as to whether the patient has congenital heart disease, a categorical indication as to whether the patient has chronic respiratory disease arising in the perinatal period, a categorical indication as to whether the patient has a chronic pulmonary disease, and a categorical indication as to whether the patient has a congenital anomaly of the respiratory system. In some embodiments, the clinical information comprises a categorical indication as to whether the patient has congenital heart disease, where, when the patient has congenital heart disease, the group of determinants further comprises a categorical indication as to whether the patient has moderate or severe pulmonary hypertension, an identity of a medication that is being given to the patient for the congenital heart disease, and/or a date when the medication for the congenital heart disease was administered to the patient.

In some embodiments, the clinical information comprises a categorical indication as to whether the patient has a chronic pulmonary disease where, when the patient has the chronic pulmonary disease, the group of determinants further comprises a categorical indication as to whether the patient receives supplemental oxygen, a categorical indication as to whether the patient receives a corticosteroid, a categorical indication as to whether the patient receives a diuretic, and/or a categorical indication as to whether the patient receives a bronchodilators. IN some embodiments, the requesting step further comprises providing an age of the patient and the receiving step comprises receiving a denial of coverage for the patient when the patient is more than two years old.

In some embodiments, the clinical information comprises at least two, at least three, at least four, or at least five determinants from the group of determinants consisting of a gestational age of the patient, a weight of the patient, a categorical indication as to whether the patient has congenital heart disease, a categorical indication as to whether the patient has chronic respiratory disease arising in the perinatal period, a categorical indication as to whether the patient has a chronic pulmonary disease, and a categorical indication as to whether the patient has a congenital anomaly of the respiratory system. In some embodiments, the clinical information comprises one or more, two or more, three or more, four or more, or five or more risk factors selected from the group consisting of a categorical indication as to whether the patient has a school age sibling, a categorical indication as to whether the patient has been subjected to an air pollutant, a categorical indication as to whether the patient attends day care, a categorical indication as to whether the patient has severe neuromuscular disease, a categorical indication as to whether the patient is subjected to crowded living conditions, a categorical indication as to whether the patient had a birth weight of less than 2500 grams, a categorical indication as to whether the patient was part of a multiple birth, a categorical indication as to whether there is a history of asthma in the patient's family, a categorical indication as to whether the patient suffers from a congenital abnormality or airway, and a categorical indication as to whether the patient has been exposed to tobacco smoke.

In some embodiments, transmittal of the prescription information and the clinical information for the patient to a remote computer is done in a packet-based form over a wide area network or Internet. In some embodiments, the prescription information and the clinical information for the patient are transmitted in a secure manner over the wide area network or Internet. In some embodiments, the prescription information and the clinical information for the patient are transmitted using the Hypertext Transport Protocol over a secure socket layer. In some embodiments, the prescription information for the patient further includes one or more, two or more, three or more, four or more, five or more, or six or more insurance information elements selected from the group consisting of identification of the primary insurer for the patient, a primary cardholder name, a primary cardholder social security number, a primary policy number, a primary insurer telephone number, a primary employer, a primary group number, an identification of a secondary insurer for the patient, a secondary cardholder name, a secondary cardholder social security number, a secondary policy number, a secondary insurer telephone number, a secondary employer, and a secondary group number.

In some embodiments, an identity of a specialty pharmacy distributor for a patient in the plurality of patients is stored in a patient record associated with the patient. In some embodiments, an identity of a drug benefit provider for a patient in the plurality of patients is stored in a patient record associated with the patient. In some embodiments, the clinical information for a patient in the plurality of patients comprises a categorical indication as to whether the patient spent time in a neonatal intensive care unit. In some embodiments, the prescription information for a patient in the plurality of patients further comprises an address where the prescription is to be shipped. In some embodiments, the method further comprises generating a schedule for when a patient in the plurality of patients should receive the predetermined pharmaceutical and storing the schedule in a patient record associated with the patient. In some embodiments, the method further comprises sending an alert to a care practitioner or patient at a time prior to when the patient is due for a dosage of the predetermined pharmaceutical as determined by the calendar. In some embodiments, the method further comprises storing an identity of each practitioner in a medical practitioner group that is responsible for making requests for prescriptions for the predetermined pharmaceutical for any of the patients in the plurality of patients.

Still another aspect provides a method for processing a request for a prescription for a predetermined pharmaceutical that requires preauthorization based upon clinical information of a patient. The method comprises obtaining prescription information for the patient, where the prescription information comprises (i) an identity of the patient, (ii) an amount of the predetermined pharmaceutical, and (iii) a prescription for the amount of the predetermined pharmaceutical. The method further comprises receiving patient clinical information, where the patient clinical information comprises one or more determinants of the patient and where each determinant in the one or more determinants contributes to a basis for authorizing or denying coverage to the patient for the predetermined pharmaceutical, and where at least one determinant in the one or more determinants is not a standardized code. The method further comprises storing the prescription information and the patient clinical information in electronic form. The method further comprises sending the prescription information and the patient clinical information to a pharmacy that is configured to use the prescription information and the patient clinical information to make a coverage decision as to whether to grant coverage to the patient for the predetermined pharmaceutical, where the coverage decision made by the pharmacy is based upon (i) a set of guidelines provided by an insurer of the patient, (ii) the prescription information, and (iii) the patient clinical information. The method further comprises communicating the coverage decision to a user interface device, a monitor, a computer-readable storage medium in tangible form, a computer-readable memory, or a local or remote computer system, or displaying the coverage decision in a user readable form.

Another aspect provides a computer-readable medium storing a computer program product, executable by a computer, to manage a plurality of patients that are each in need of a predetermined pharmaceutical that requires preauthorization based upon patient clinical data. The computer program product comprises instructions for obtaining prescription information for each respective patient in the plurality of patients, where the prescription information comprises an identity of the respective patient and an amount of the predetermined pharmaceutical that has been prescribed to the patient. The computer program product further comprises instructions for receiving clinical information associated with each respective patient in the plurality of patients, where the clinical information for each respective patient comprises one or more determinants and where each determinant in the one or more determinants contributes to a basis for authorizing or denying coverage to the respective patient for the predetermined pharmaceutical, and where at least one determinant in the one or more determinants is not a standardized code. The computer program product further comprises instructions for requesting coverage for a patient in the plurality of patients for the predetermined pharmaceutical by transmitting the prescription information and the clinical information to a specialty pharmaceutical distributor at a remote location by electronic means. The computer program product further comprises instructions for receiving a grant or denial of coverage for a patient in the plurality of patients for the predetermined pharmaceutical. The computer program product further comprises instructions for storing the grant or denial of coverage for the patient in a record associated with the patient.

Still another aspect provides an apparatus for managing a plurality of patients that are each in need of a predetermined pharmaceutical that requires preauthorization based upon patient clinical data. The apparatus comprises a processor and a memory, coupled to the processor. The memory stores a module comprising instructions for obtaining prescription information for each respective patient in the plurality of patients, where the prescription information comprises an identity of the respective patient and an amount of the predetermined pharmaceutical that has been prescribed to the patient. The module further comprises instructions for receiving clinical information associated with each respective patient in the plurality of patients, where the clinical information for each respective patient comprises one or more determinants and where each determinant in the one or more determinants contributes to a basis for authorizing or denying coverage to the respective patient for the predetermined pharmaceutical. At least one, two, three, four, for five determinants in the one or more determinants is not a standardized code. The module further comprises instructions for requesting coverage for a patient in the plurality of patients for the predetermined pharmaceutical by transmitting the prescription information and the clinical information to a specialty pharmaceutical distributor at a remote location by electronic means. The module further comprises instructions for receiving a grant or denial of coverage for a patient in the plurality of patients for the predetermined pharmaceutical. Further still, the module comprises instructions for storing the grant or denial of coverage for the patient in a record associated with the patient.

BRIEF DESCRIPTION OF THE DRAWINGS

FIG. 2 illustrates an electronic form for entering and reviewing general demographic details of a patient in accordance with an embodiment of the present invention.

FIG. 3 illustrates an electronic form for entering and reviewing primary insurance information of a patient in accordance with an embodiment of the present invention.

FIG. 4 illustrates an electronic form for entering and reviewing drug benefit manager insurance information of a patient in accordance with an embodiment of the present invention.

FIG. 5 illustrates an electronic form for entering specialty pharmacy distributor information of a patient in accordance with an embodiment of the present invention.

Figure 6:
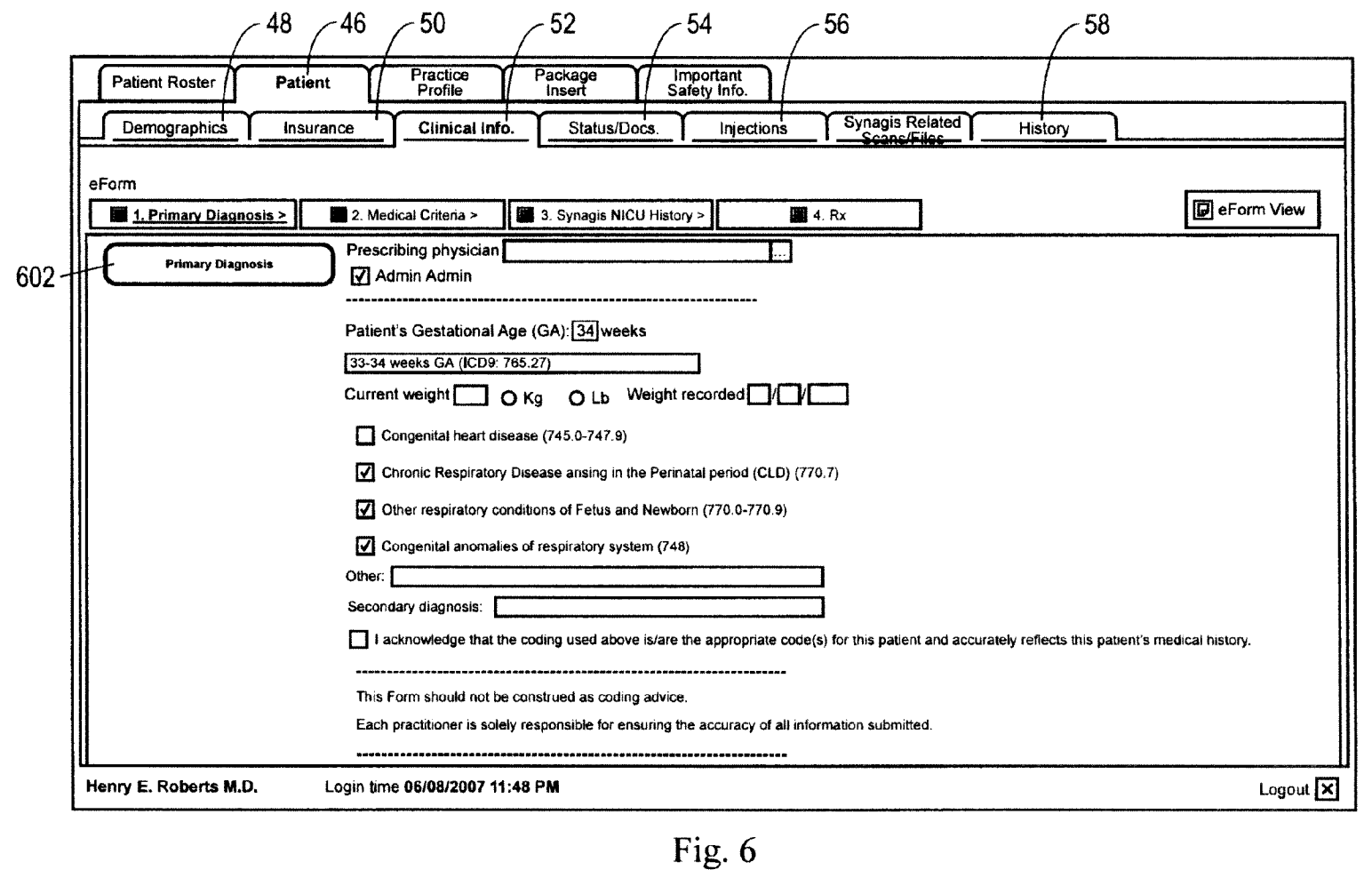

FIG. 6 illustrates an electronic form for entering a primary diagnosis for a patient in need of a specialty pharmaceutical in accordance with an embodiment of the present invention.

FIG. 7 illustrates an electronic form for entering clinical information associated with a primary diagnosis for a patient in need of a specialty pharmaceutical in accordance with an embodiment of the present invention.

FIG. 10 illustrates an electronic form for entering other medical criteria of a patient in need of a specialty pharmaceutical that may be of use to an insurer for approving a prescription for the specialty pharmaceutical for the patient in accordance with an embodiment of the present invention.

FIGS. 13B and C collectively illustrate an exemplary prescription for a specialty pharmaceutical that is generated by a pharmaceutical online tracking module and includes at least some noncoded clinical data that can be used by an insurer to deny or approve coverage for the specialty pharmaceutical in accordance with an embodiment of the present invention.

FIG. 14 illustrates a form for entering status management information for a specialty pharmaceutical dosage regimen in accordance with an embodiment of the present invention.

FIG. 16 illustrates a dosage regimen (calendar) for administration of a clinical pharmaceutical to a patient that is stored in a patient record associated with the patient in accordance with an embodiment of the present invention.

FIG. 20 illustrates a form for specifying the location of a medical practice that oversees the prescribing and administration of specialty pharmaceuticals to patients in accordance with an embodiment of the present invention.

FIG. 22 illustrates a form for specifying the contact information of a medical care giver at a medical practice that oversees the prescribing and administration of specialty pharmaceuticals to patients in accordance with an embodiment of the present invention.

FIG. 23 illustrates a form for specifying the contact information of a medical care giver at a medical practice that oversees the prescribing and administration of specialty pharmaceuticals to patients in accordance with an embodiment of the present invention.

FIG. 26 illustrates a form for providing a roster of the patients that receive specialty pharmaceutical care at a medical practice group in accordance with an embodiment of the present invention.

Like reference numerals refer to corresponding parts throughout the several views of the drawings.

DETAILED DESCRIPTION

Systems and methods that address the shortcomings found in the prior art are provided. One embodiment provides is a web-based tool that physicians can use to store patient information, send out clean and complete requests for specialty pharmaceuticals to specialty pharmacists and, in general, manage their specialty pharmaceuticals patients. Using the systems and methods disclosed herein alleviates the need for paper-based forms and provides a convenient web-based method for electronic prior authorization of specialty pharmaceuticals.

Figure 1:
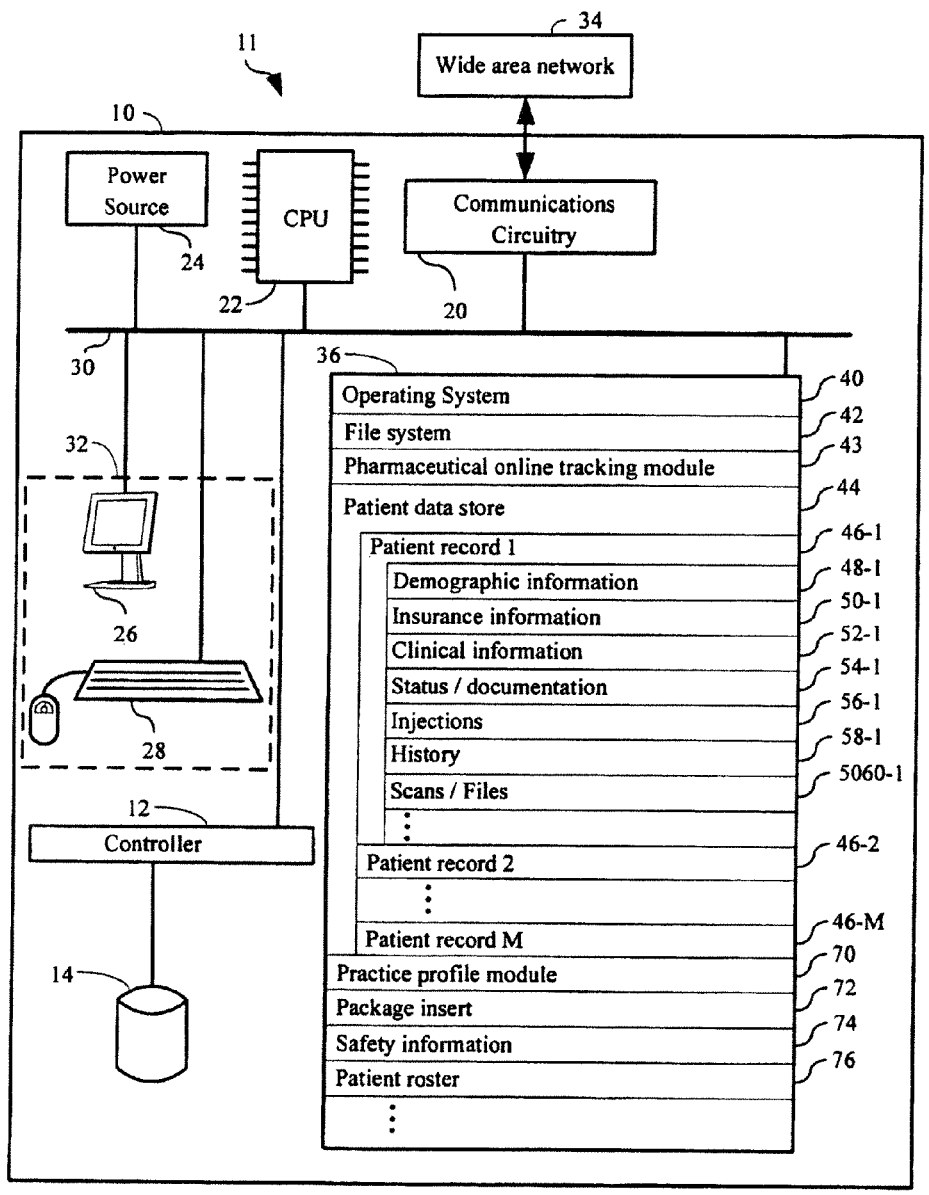
FIG. 1 illustrates an exemplary computer system for providing specialty pharmaceuticals in accordance with an embodiment of the present invention.

FIG. 1 details an exemplary system 11 for providing specialty pharmaceuticals. The system preferably comprises a computer system 10 having:
- a central processing unit 22;
- a main non-volatile storage unit 14, for example a hard disk drive, for storing software and data, the storage unit 14 controlled by storage controller 12;
- a system memory 36, preferably high speed random-access memory (RAM), for storing system control programs, data, and application programs, comprising programs and data loaded from non-volatile storage unit 14; system memory 36 may also include read-only memory (ROM);

a user interface 32, comprising one or more input devices (e.g., keyboard 28, a mouse) and a display 26 or other output device;

a network interface card 20 (communications circuitry) for connecting to any wired or wireless communication network 34 (e.g., a wide area network such as the Internet);

a power source 24 to power the aforementioned elements; and an internal bus 30 for interconnecting the aforementioned elements of the system. Operation of the computer 10 is controlled primarily by the operating system 40, which is executed by the central processing unit 22. The operating system 40 can be stored in the system memory 36. In a typical implementation, the system memory 36 also includes:

a file system 42 for controlling access to the various files and data structures used by the present invention;

a pharmaceutical online tracking module 43 for assisting medical professionals with requests for specialty pharmaceuticals;

a patient data store 44 for confidentially storing information about patients in need of specialty pharmaceuticals such as patient demographic information 48, insurance information 50, clinical information 52, status/documentation 54, injections 56, specialty pharmaceutical use history 58; and other documents 5060 associated with patients;

a practice profile module 70 for storing practice information;

one or more package inserts 72 for each of the specialty pharmaceuticals tracked by pharmaceutical online tracking module 43;

safety information 74 for each of the specialty pharmaceuticals tracked by pharmaceutical online tracking module 43; and a patient roster 76 for providing the details of each patient handled by a physician or a physician practice group supported by pharmaceutical online tracking module 43.

As illustrated in FIG. 1, computer 10 comprises a patient data store 44. Patient data store 44 can be any form of data storage system including, but not limited to, a flat file, a relational database (SQL), or an on-line analytical processing (OLAP) database (MDX and/or variants thereof). In some specific embodiments, patient data store 44 is a hierarchical OLAP cube. In some specific embodiments, patient data store 44 comprises a star schema that is not stored as a cube but has dimension tables that define hierarchy. Still further, in some embodiments, patient data store 44 has hierarchy that is not explicitly broken out in the underlying database or database schema (e.g., dimension tables that are not hierarchically arranged). In some embodiments, patient data store 44 is a single database that includes patient records 46. In other embodiments, the patient data store 44 in fact comprises a plurality of databases that may or may not all be hosted by the same computer 10. In such embodiments, some components of the patient data store 44 are stored on computer systems that are not illustrated by FIG. 1 but that are addressable by the wide area network 34.

In some embodiments, the data store 44 and related software modules illustrated in FIG. 1 (e.g. pharmaceutical online tracking module 43, practice profile module 70, package insert 72, safety information 74, and patient roster 76) are on a single computer (e.g., computer 10) and in other embodiments patient data store 44 and related software modules illustrated in FIG. 1 are hosted by several computers (not shown). In fact, any arrangement of the patient data store 44 and the software and/or data modules illustrated in FIG. 1 on one or more computers is within the scope of the present invention so long as these components are addressable with respect to each other across the network 34 or by other electronic means. Thus, the present invention fully encompasses a broad array of computer systems.

Figure 2:
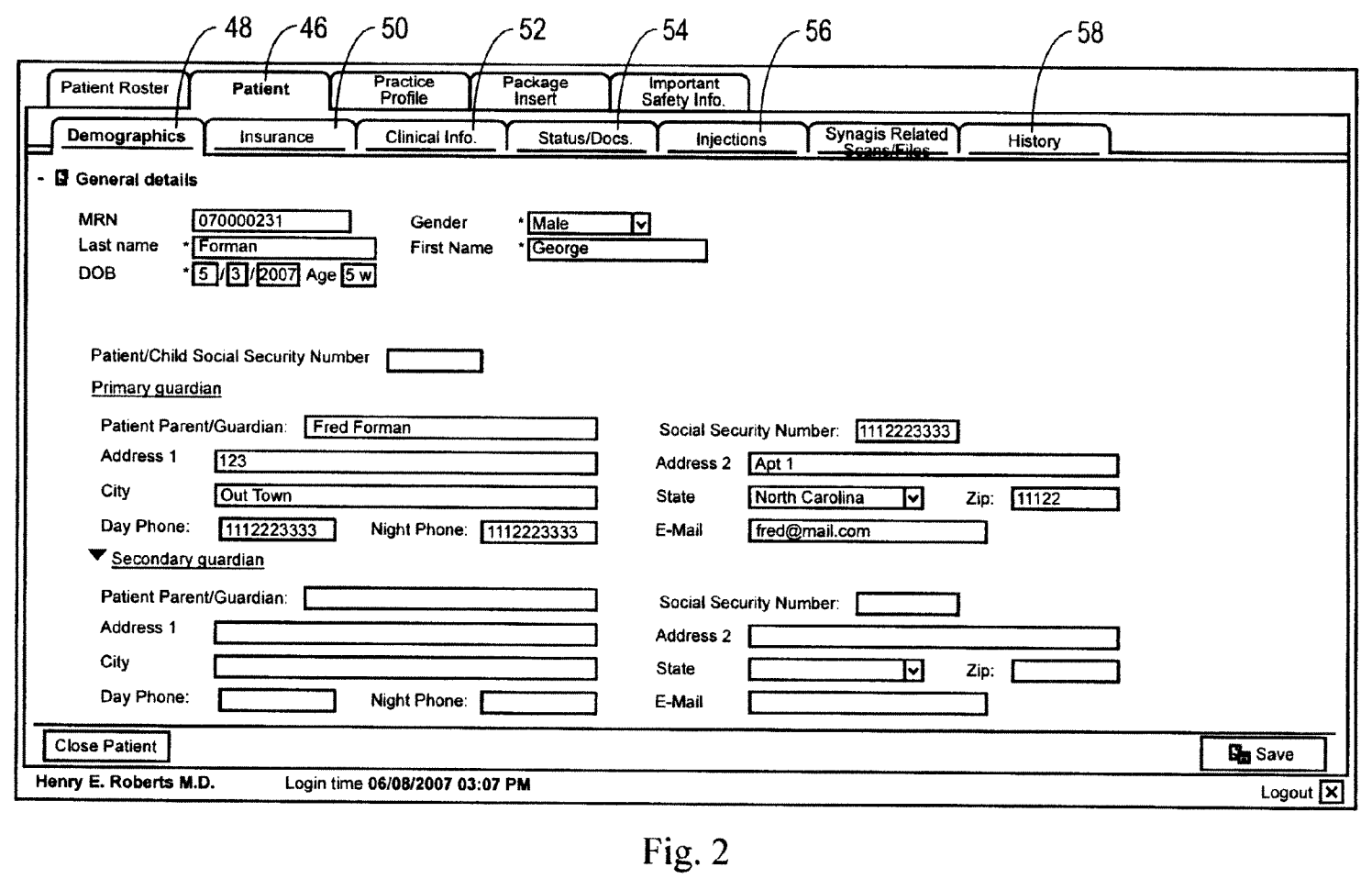

Provided are systems and methods that help physicians that have specialty pharmaceutical patients to manage such patients. There are a number of aspects involved in managing such patients. One aspect is maintenance of a record 46 of all the information about that patient. Such information includes, but is not limited to, patient demographic information 48, insurance information 50, clinical information 52, status/documentation 54, injections 56, specialty pharmaceutical use history 58, and other documents 5060 relating to the patient. Referring to FIG. 2, exemplary demographic information 48 includes, but is not limited to, any combination of an MRN number, gender, last name, first name, date of birth, patient social security number, name of primary guardian, social security number of primary guardian, address of primary guardian, phone number of primary guardian, E-mail address of primary guardian, name of secondary guardian, social security number of secondary guardian, address of secondary guardian, phone number of secondary guardian, and/or E-mail address of secondary guardian.

Figure 3:
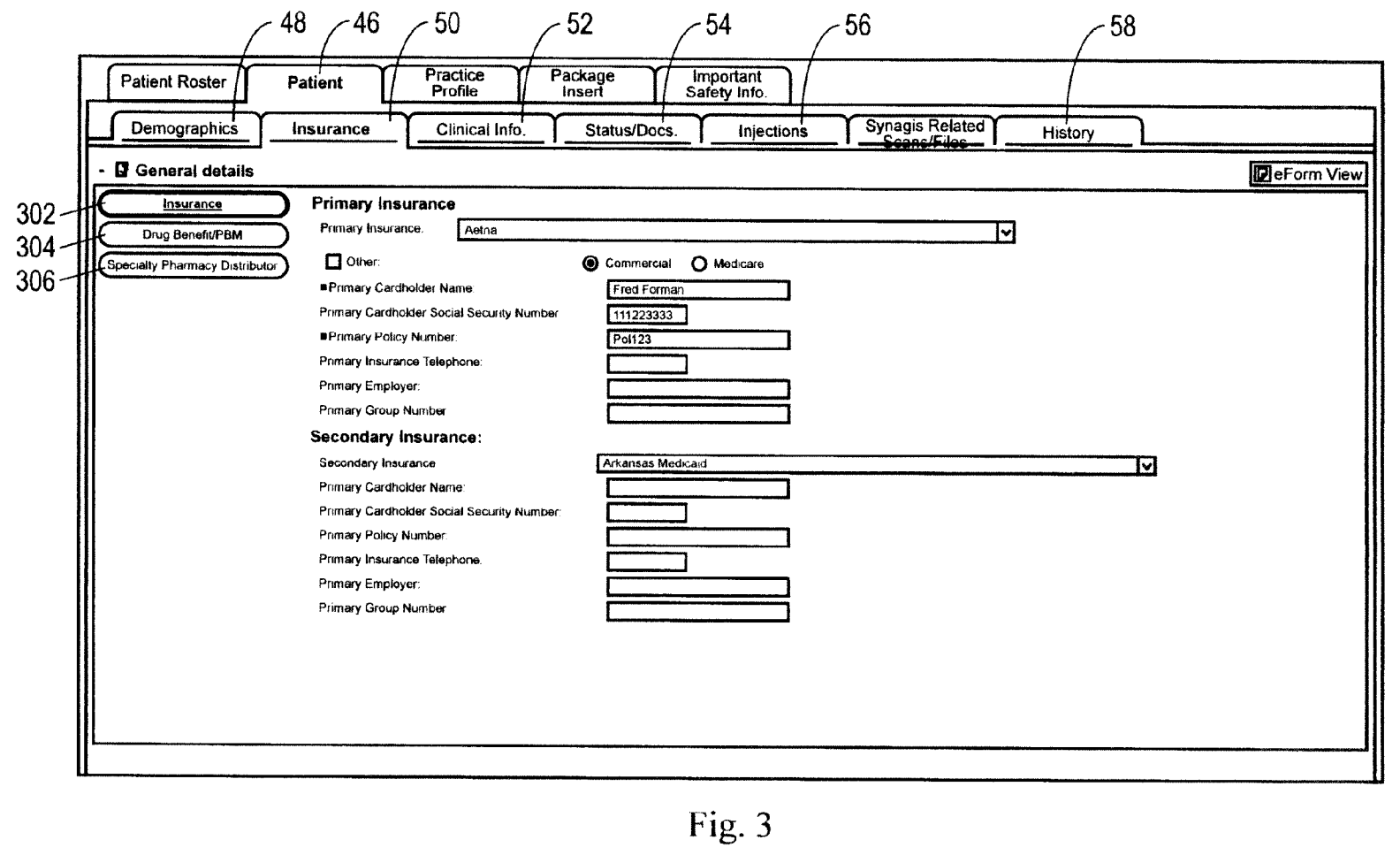

Referring to FIG. 3, there are three classes of exemplary insurance information 50 views provided by an exemplary embodiment of pharmaceutical online tracking module 43. They are an insurance view 302, a drug benefit/primary benefit manager (PBM) view 304 and a specialty pharmacy distributor view 306. In FIG. 3, the insurance view 302 has been selected. As illustrated in FIG. 3, the insurance view 302 provides fields that include, but are not limited to, any combination of an identification of the primary insurer for a given patient, an indication of whether the primary insurer is commercial or Medicaid, the primary cardholder name, the primary cardholder social security number, the primary policy number, the primary insurer telephone number, the primary employer, the primary group number, an identification of the secondary insurer for a given patient, an indication of whether the secondary insurer is commercial or Medicaid, the secondary cardholder name, the secondary cardholder social security number, the secondary policy number, the secondary insurer telephone number, the secondary employer, and the secondary group number.

Figure 4:
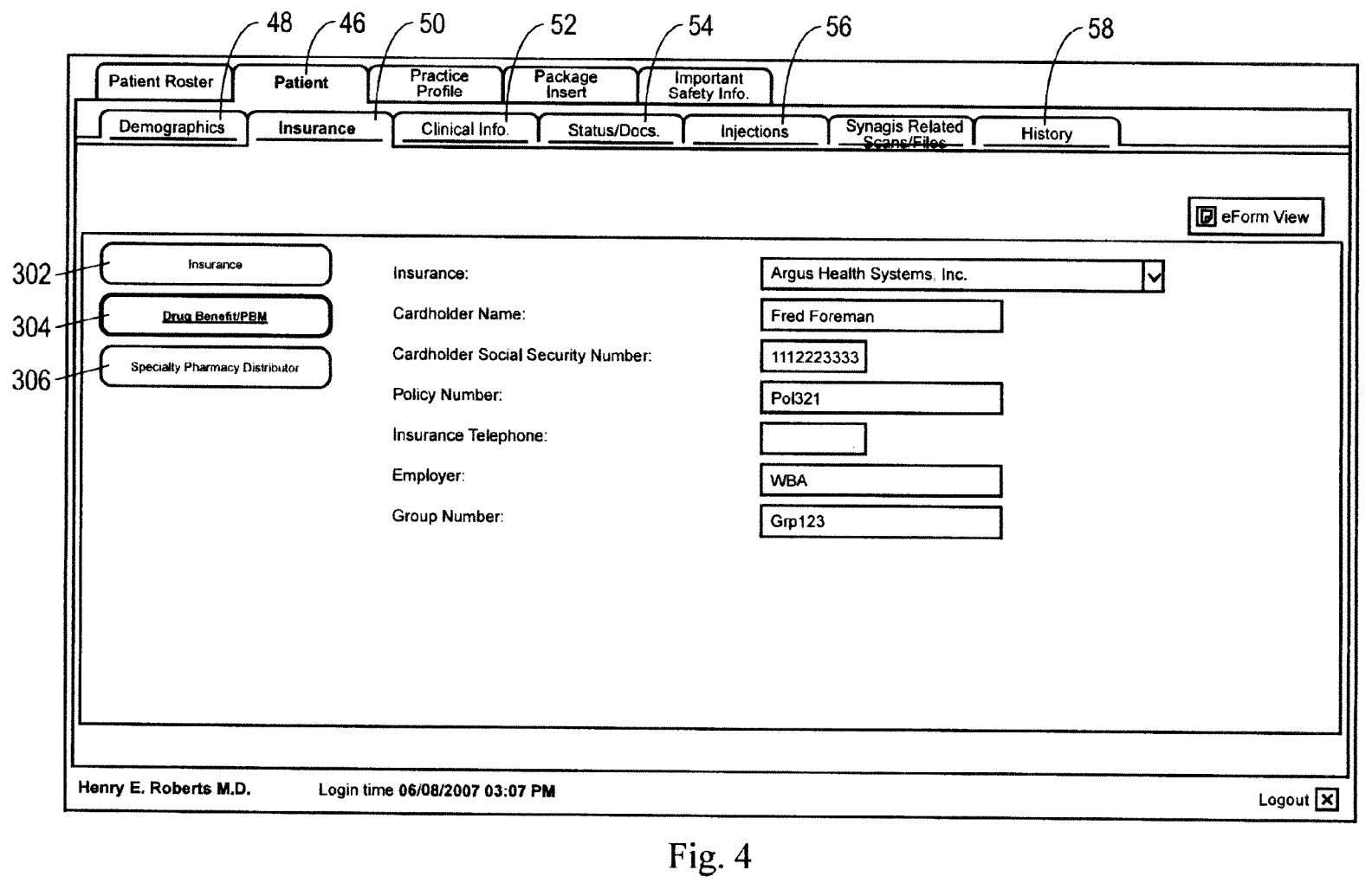
Figure 5:
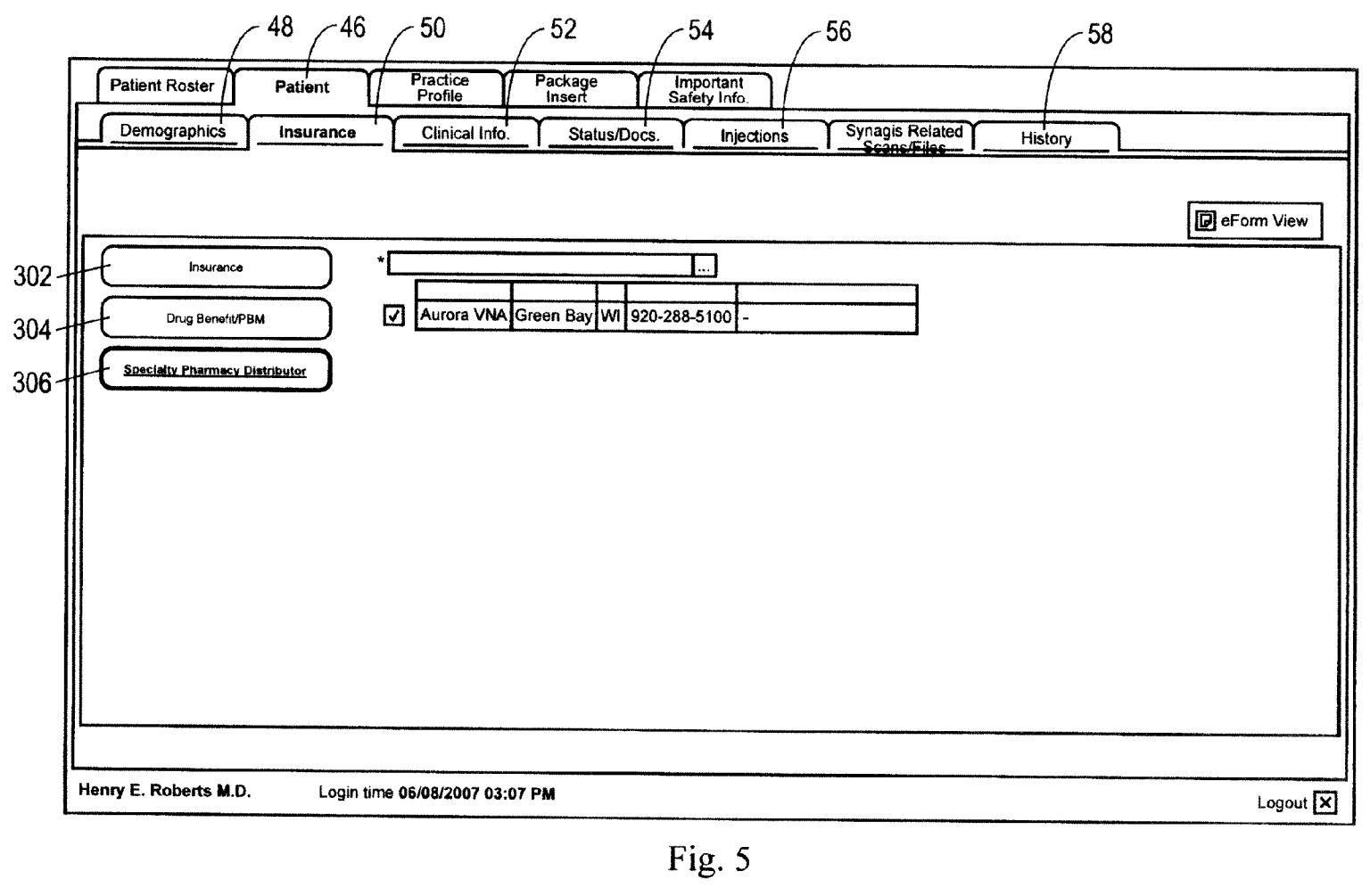

In FIG. 4, the drug benefit/PBM view 304 has been selected. As illustrated in FIG. 4, the drug benefit/PBM view 304 provides information about any drug prescription plan that the patient may have. In FIG. 4, the drug benefit/PBM view 304 provides fields that include, but are not limited to, any combination of the identity of the drug benefit/PBM provider for the patient, the cardholder name of the drug benefit/PBM policy, the cardholder social security number, the policy number, the insurance telephone number, the employer of the drug benefit/PBM cardholder, and/or the group number. Advantageously, referring to FIG. 5, the specialty pharmacy distributor view 306 allows for the association of one or more specialty pharmacy distributors with a patient. Each patient's prescription for a specialty pharmaceutical such as SYNAGIS® is submitted to a single specialty pharmacy distributor usually. In some instances, the prescription could be submitted to more than one specialty pharmacy distributors but this is not typical. For instance, there are some instances where the prescription goes to a particular specialty pharmacy distributor that, due to contractual constraints with the patient's insurance provider, cannot service the prescription. In such instances, the first specialty pharmacy distributor refers the prescription to somebody else. Advantageously, specialty pharmacy distributor view 306 provides a mechanism for tracking the specialty pharmacy distributor that a patient's specialty pharmaceutical has been referred to in order to make sure that once a prescription has been sent out, the prescription is filled in a more automated fashion.

Figure 7:
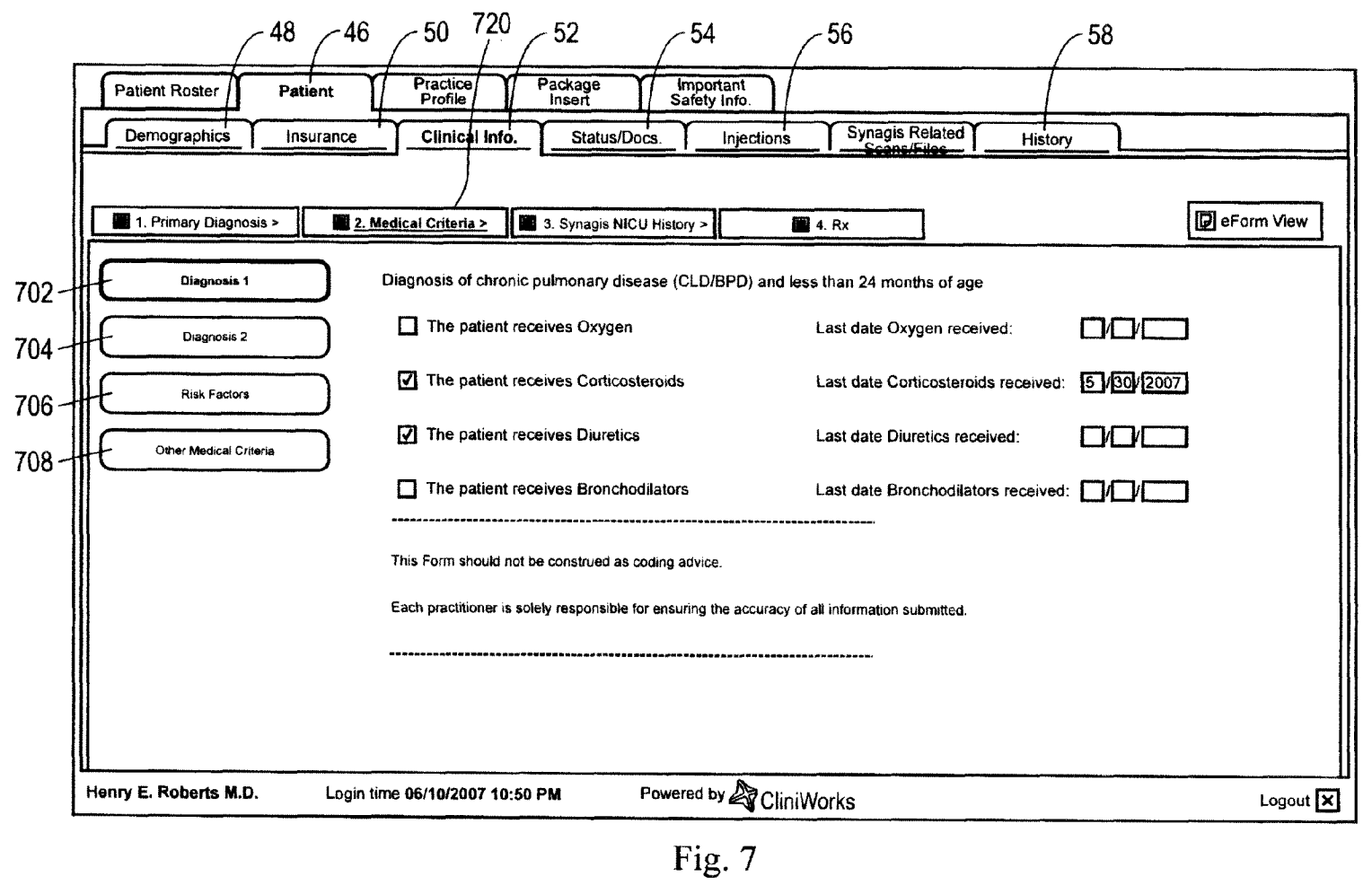

Referring to FIGS. 6 through 10, pharmaceutical online tracking module 43 enables physicians to maintain clinical information 52 about specialty pharmaceutical patients. Any of the information entered using the electronic forms illustrated in FIG. 6 through 10 are considered clinical information 52. FIGS. 6 through 10 are particularly directed to medical factors that provide a determination as to whether a patient is a good candidate for SYNAGIS®. However, there is no requirement that clinical information 52 tracked by online tracking module 43 be limited to SYNAGIS®. The medical factors for SYNAGIS® are given to illustrate the type of clinical information that can advantageously be tracked as clinical information 52 in online tracking module 43. Thus, specifically referring to FIG. 6, factors that lead to a primary diagnoses 602 that a patient will be a good candidate for SYNAGIS® are provided. These factors include the patient's gestational age, current weight, whether the patient has congenital heart disease, chronic respiratory disease arising in the perinatal period, other respiratory conditions of the fetus or newborn, or congenital anomalies of the respiratory system. For each of the medical factors identified in the primary diagnosis (congenital heart disease, chronic respiratory disease, etc.), there is an associated medical criteria form that can be used to easily retrieve and store medical criteria associated with the medical factor. For example, in FIG. 6 the patient has been indicated to have chronic respiratory disease. Thus, correspondingly, in FIG. 7, an associated form is provided to enter medical criteria related to the condition of chronic pulmonary disease. The form illustrated in FIG. 7 is accessed by clicking on the "Medical Criteria" tab 720 and selecting tab 702 "diagnosis 1." For chronic pulmonary disease, in the illustrative embodiment shown in FIG. 7, the form can be used to indicate whether the patient receives oxygen, corticosteroids, diuretics, and bronchodilators and the last date for which each of these medications. Tabs 702 through 708 will vary depending on the primary diagnosis made in the form illustrated in FIG. 6.

Figure 8:
FIG. 8 illustrates an electronic form for entering clinical information associated with a secondary diagnosis for a patient in need of a specialty pharmaceutical in accordance with an embodiment of the present invention.
Figure 9:
FIG. 9 illustrates an electronic form for entering risk factors of a patient in need of a specialty pharmaceutical in accordance with an embodiment of the present invention.
Figure 10:
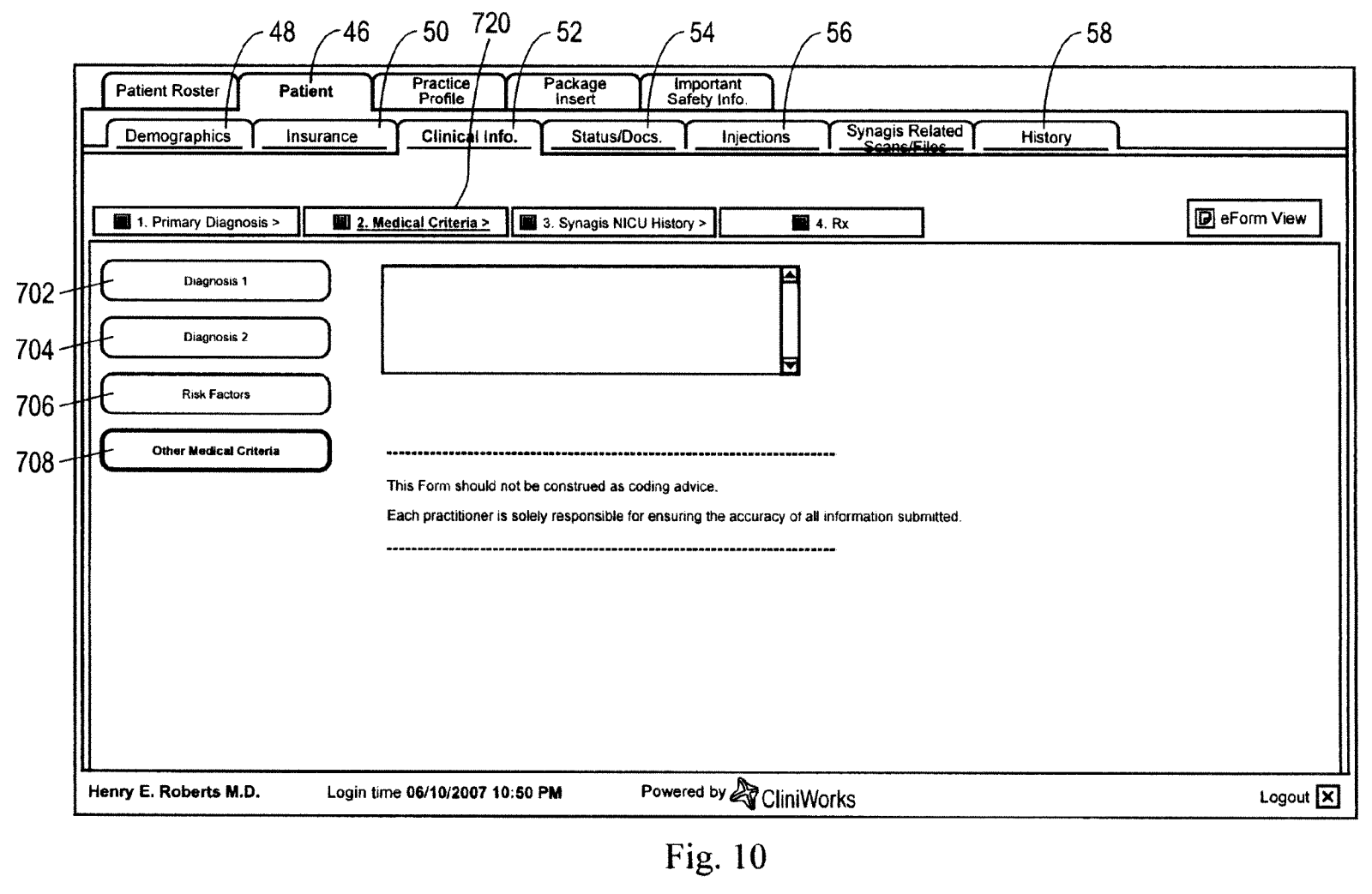

In the exemplary embodiment based upon the diagnosis provided in the form illustrated in FIG. 7, when tab 704 is selected, information associated with a diagnosis of hemodynamically significant congenital heart disease (CHD) at 24 and less months of age may be entered as illustrated in FIG. 8. Such information includes an indication as to whether the patient has diagnosis of moderate to severe pulmonary hypertension, medications being given for CHD, and the last date received. Referring to FIG. 9, in the case of SYNAGIS®, risk factors that make a patient a better candidate for the pharmaceutical may be entered by selecting tab 706. As illustrated in FIG. 9, these risk factors include whether the patient has a school-age sibling, whether the patient has been subjected to an air pollutant, whether the patient attends day care, whether the patient has severe neuromuscular disease, whether the patient is subject to crowded living conditions, whether the patient had a birth weight of less than 2500 grams, whether the patient was part of a multiple birth, whether there is a history of asthma in the patient's family, whether the patient suffers from a congenital abnormality or airway, and whether the patient has been exposed to tobacco smoke (e.g., the patient has family members that smoke). Referring to FIG. 10, the practitioner can enter and store other medical criteria of the practitioner's choosing by selecting tab 708.

The ability to enter, store and retrieve medical criteria in forms tailored to particular specialty pharmaceuticals as illustrated in FIGS. 6 through 10 is highly advantageous. Such information is highly varied from patient to patient and yet is the predominant determining factor considered by insurers when authorizing a prescription of a specialty pharmaceutical. Thus, given a particular patient's insurance policy, certain of the information illustrated in exemplary FIGS. 6 through 10 either needs to be present or otherwise accounted for in order for the patient to be approved for treatment. In the case of specialty pharmaceuticals other than SYNAGIS®, other medical criteria may be provided through forms that are equivalent to the forms illustrated in FIGS. 6 through 10.

Figure 11:
FIG. 11 illustrates an electronic form for entering neonatal intensive care unit (NICU) history and information regarding whether SYNAGIS® was administered in the NICU in accordance with an embodiment of the present invention.

Referring to FIG. 11, pharmaceutical online tracking module 43 allows the medical practitioner to attach a history from the time that this patient may have stayed in a neonatal intensive care unit. Thus, if the patient was premature or had other complications that caused the patient to be in a neonatal intensive care unit, an indication that the patient spent time is indicated by selecting the "NICU history" tab 1102 which pulls up the form illustrated in FIG. 11. Furthermore, the NICU discharge summary can be attached using the scans/files tab 60. More details on scans/file tab 60 are provided below in conjunction with FIG. 17.

Figure 12:
FIG. 12 illustrates a form for entering specialty pharmaceutical delivery instructions for a prescription to a specialty pharmaceutical in accordance with an embodiment of the present invention.
Figure 13A:
FIG. 13A illustrates a form for entering a prescription for a specialty pharmaceutical in accordance with an embodiment of the present invention.

Referring to FIGS. 12 and 13A, pharmaceutical online tracking module 43 allows the medical practitioner to generate a prescription (an Rx) through tab 1202. In FIG. 12, delivery instructions can be entered when table 1302 is selected. Such delivery instructions can include, in the case of SYNAGIS®, an indication as to whether an agency nurse is to visit the home of the subject to deliver the pharmaceutical and, if so the agency name. Such delivery instructions can further include the expected date for the first or next injection. Such deliver instructions can further indicate whether the specialty pharmaceutical is to be shipped to the practitioner's office, the patient's home, or a clinic. If a clinic is selected the form illustrated in FIG. 12 further allows for the provision of the clinic's address. Pharmaceutical online tracking module 43 allows for the storage of man different addresses, any of which can be selected by the medical practitioner as the delivery address of the specialty pharmaceutical. FIG. 12 gives exemplary prompts for information suitable for generating delivery instructions for a SYNAGIS® prescription. However, the invention is not so limited. FIG. 12 merely serves to provide an example of the types of delivery information that may be given for a specialty pharmaceutical. Other delivery information suitable for other specialty pharmaceuticals may be implemented in one or more forms equivalent to the form shown in FIG. 12 and all such forms are within the scope of the present invention. As illustrated in FIG. 13A, tab 1302 provides a form for the actual prescription of the special pharmaceutical, in this case SYNAGIS®. Provided in the form illustrated in FIG. 13 is toggle box for prescribing SYNAGIS® liquid solution, a number of refills, and a toggle box for prescribing Epinephrine. Further provided in the form illustrated in FIG. 13A is a field to place known allergies of the patient. Advantageously by simply clicking button 1306, the prescription is sent to the specialty pharmacists. While button 1306 indicates that the prescription is sent by FAX, the invention is not so limited. In some embodiments, the prescription is sent in encrypted form over the Internet (e.g., secure Internet protocol, Hypertext Transport Protocol over a secure socket layer). Alternatively, by clicking button 1308, the prescription can be printed out and communicated to the specialty pharmacists by mail or other means.

FIGS. 13B and 13C illustrates the actual output in an exemplary embodiment that is sent to a specialty distributor when a care practitioner makes a request for a specialty pharmaceutical such as SYNAGIS®. As can be seen from FIGS. 13B and 13C, the present invention provides significant ability to provide clinical information that is simply not found in a conventional prescription such as one that a patient would get from their physician and have filled at a standard pharmacy such as WALGREENS® or other retail outlet. Advantageously, the document illustrated in FIGS. 13B and 13C provides the clinical information that is necessary to pre-authorize a SYNAGIS® patient. At the very bottom of the document, in FIG. 13C, is the prescription information that will allow that specialty pharmacy to dispense the SYNAGIS® liquid solution, 15 mgs per kilogram, with six refills. The provider name is given and there are provisions for a signature. The clinical information provided in the document illustrated in FIGS. 13B and 13C is not capable of being transmitted through a conventional e-prescribing system because such systems are hardwired and standards-based in terms of patient information, insurance, clinical information and ship to addresses. The clinical information communicated in FIGS. 13B and 13C is outside e-prescribing standards. Advantageously, in some embodiments, several or all of the fields in FIGS. 13B and 13C can be electronically uploaded at the specialty distributor once they have been transmitted to the specialty distributor. Thus, in some embodiments pharmaceutical online tracking module 43 has the ability to send the form depicted in FIGS. 13B and 13C straight from the physician's and/or clinical practice's desktop to the specialty distributor as opposed to actually having to print out a hard copy and send it. In some embodiments, a digital signature can be affixed to the prescription to facility such an electronic transfer. In some embodiments, specialty distributors are provided with a software toolkit that allows them to decode prescriptions sent by pharmaceutical online tracking module 43 so that the prescription information is directly transferred to specialty distributor servers.

Figure 14:
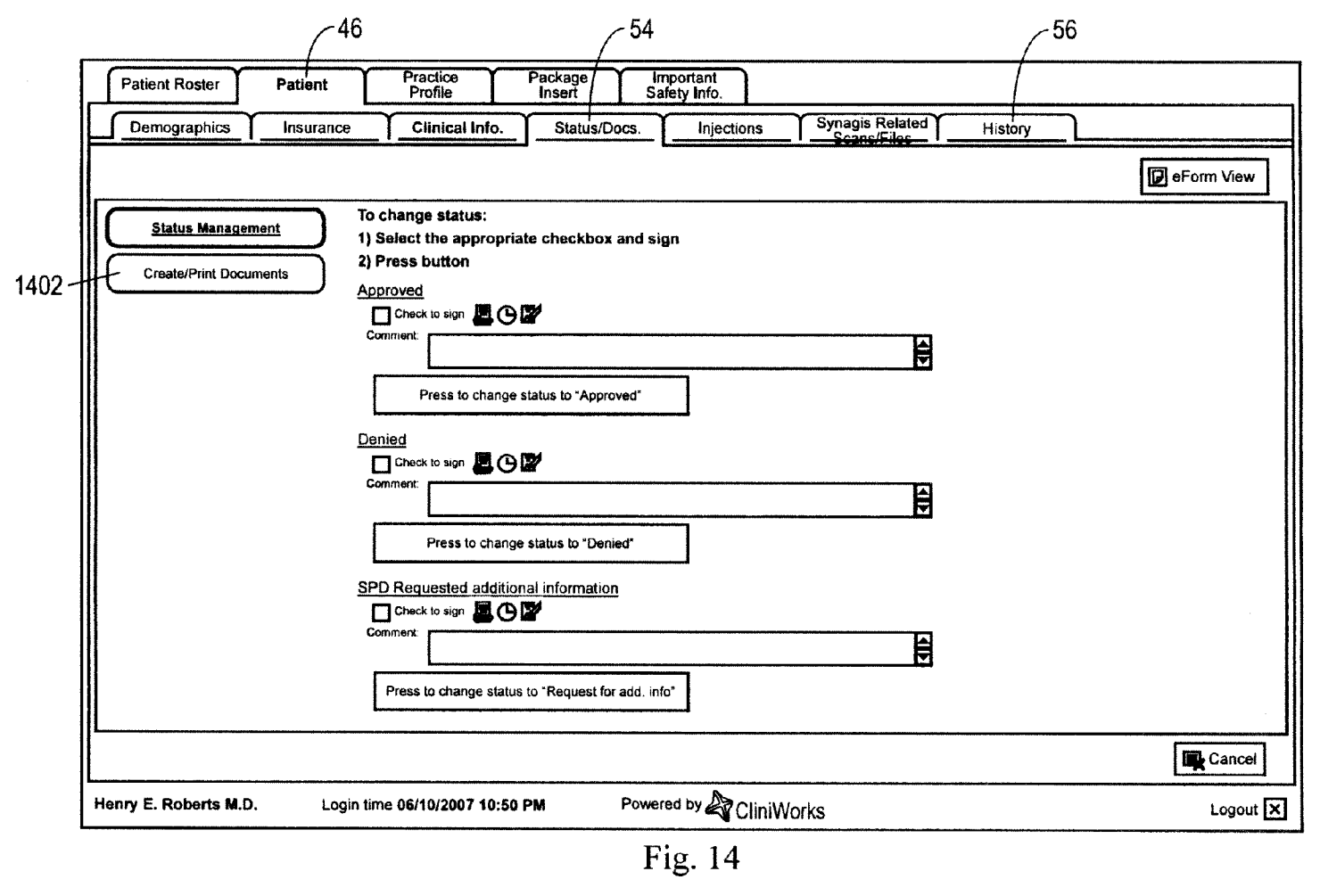
Figure 15:
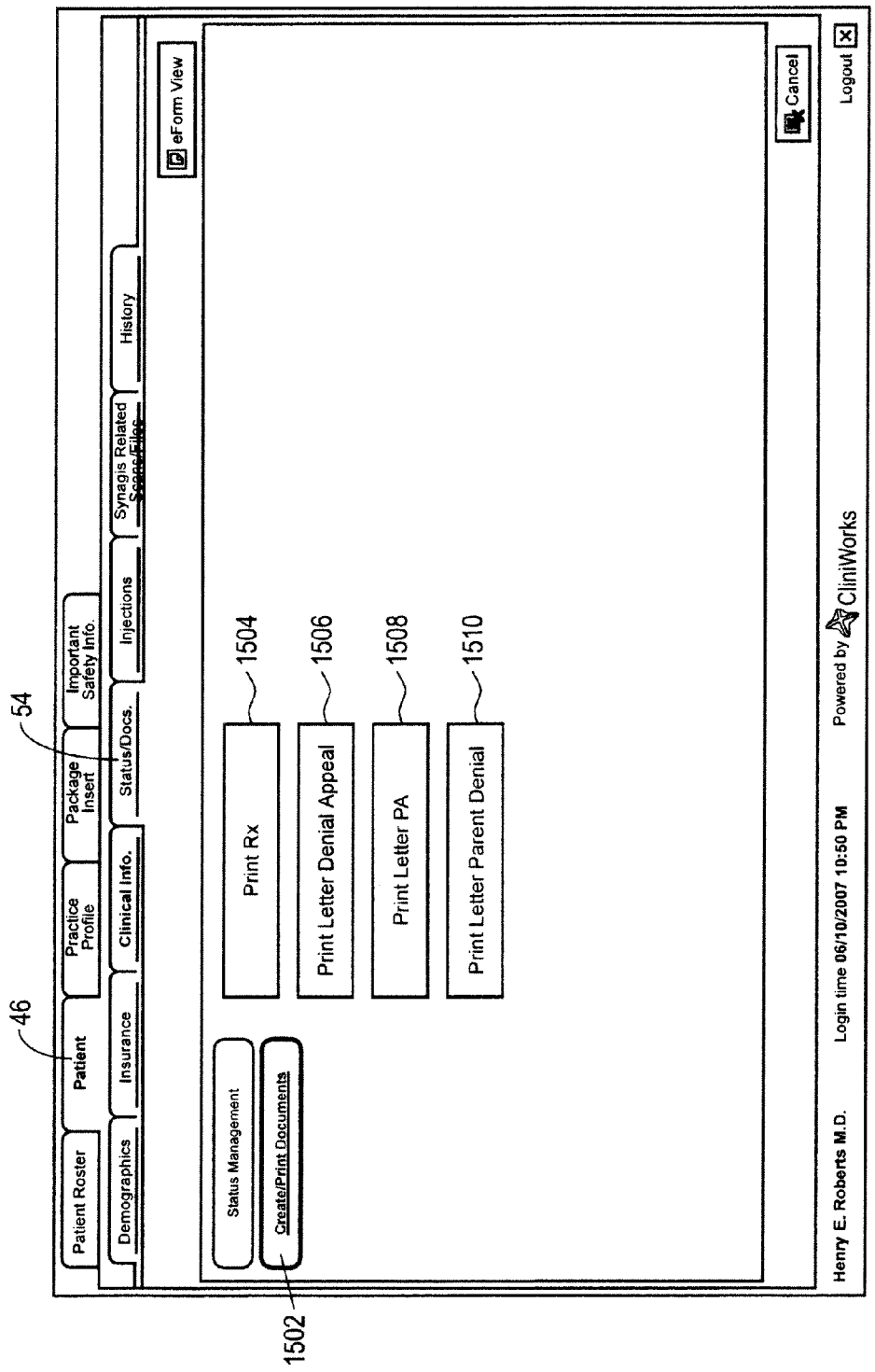
FIG. 15 illustrates a form for generation documents related to a specialty pharmaceutical including a prescription, a letter appealing denial of a prescription to a specialty pharmaceutical, a letter directed to the specialty pharmaceutical patient, and a letter to the parent of the patient indicating a denial of prescription for a specialty pharmaceutical in accordance with an embodiment of the present invention.

Referring to FIGS. 14 and 15, pharmaceutical online tracking module 43 provides physicians with additional tools for managing specialty pharmaceutical patients. Specifically, status/documentation records 54 within the patient records of patient data store 44 allows for the ability to maintain the status of each patient. Referring to FIG. 14, such information can include, for example, whether the patient was approved by an insurance company, denied by an insurance company, or whether the specialty pharmaceutical provider has asked for more information on behalf of an insurance company. An indication as to whether the patient was approved, denied, or more information is needed can be given by checking the appropriate corresponding toggle box in the form illustrated in FIG. 14. The form illustrated in FIG. 14 is given when status management tab 1402 is selected. Referring to FIG. 15, useful functionality for the practitioner is provided when tab 1502 "create/print documents" is selected. The practitioner can print the prescription by pressing tab 1504. Also, advantageously, by pressing tab 1506, the practitioner can print out a standard appeal letter in cases where the patient's prescription for the specialty pharmaceutical was denied by an insurance company. Such a letter is useful for outlining and emphasizing extenuating circumstances that the insurance company may want to consider during an appeal. Toggles 1508 and 1510 advantageously assist the practitioner in creating other types of letters, such as a letter to the parent of the patient when there has been a denial of coverage.

Figure 16:
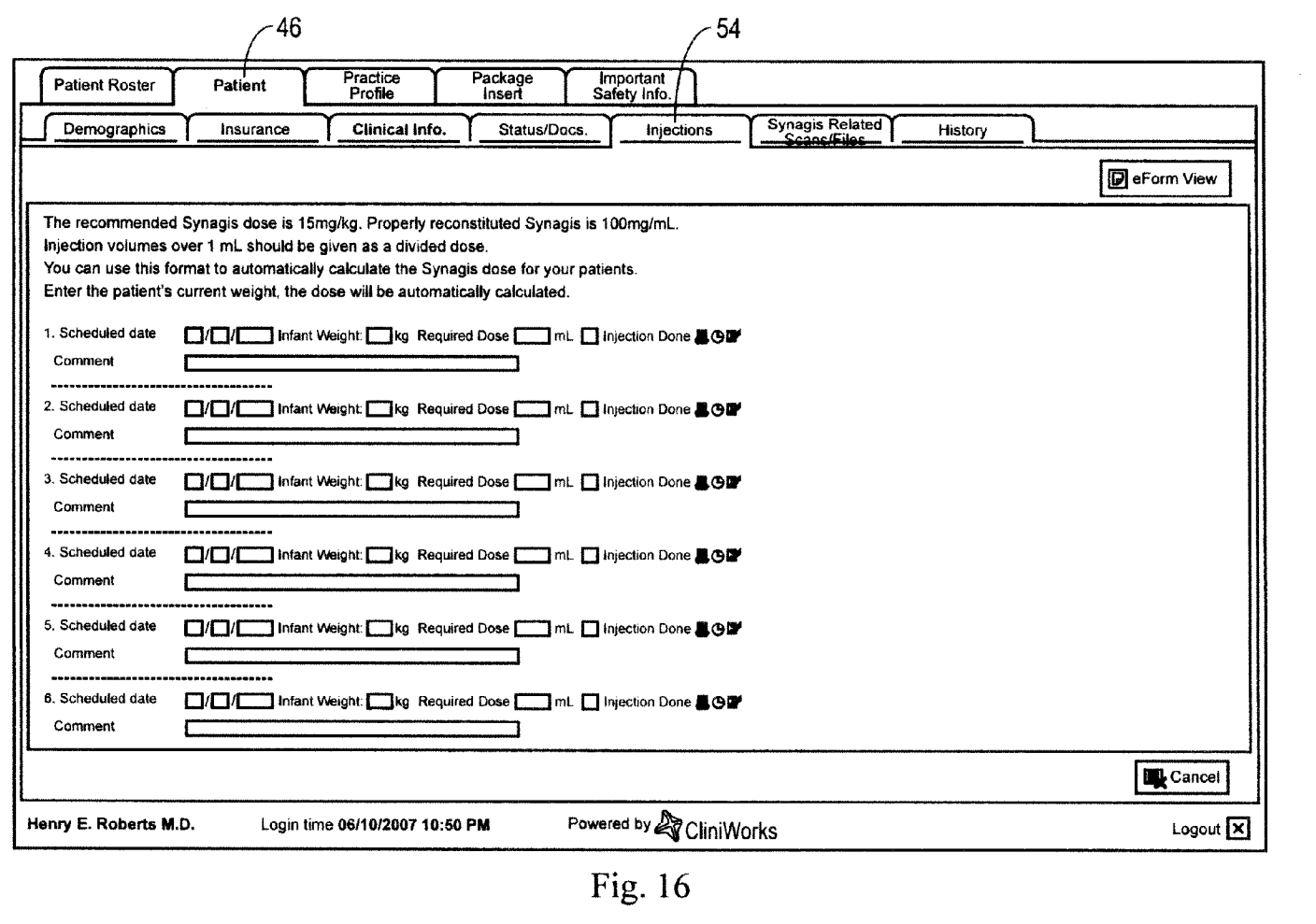

Referring to FIG. 16, pharmaceutical online tracking module 43 allows practitioners to maintain a history of when the specialty pharmaceutical was administered by selecting injections tab 56, which corresponds to injections record 56 stored in patient data store 44. As in the case of other forms illustrated herein, FIG. 16 uses the case of SYNAGIS® to illustrate some aspects of the present invention. Other records equivalent to injections record 56 can be used for other forms of specialty pharmaceuticals and such functionality is within the scope of the present invention. In FIG. 16, recommended dosage information is giving for SYNAGIS® and the practitioner can enter the date when each SYNAGIS® dosage was administered. Furthermore, for each administration of SYNAGIS® in a treatment regimen, the practitioner can enter information such as the scheduled date of administration, the infant's weight, the required dosage, whether the injection has been administered, and comments if any. The injections record 56 is highly advantageous because SYNAGIS® should be administered about every 28 to 30 days. Thus, practitioners can use the injections record 56, and equivalent records for specialty pharmaceutical other than SYNAGIS® can be used to determine when to schedule patients for administration of the specialty pharmaceuticals.

Figure 17:
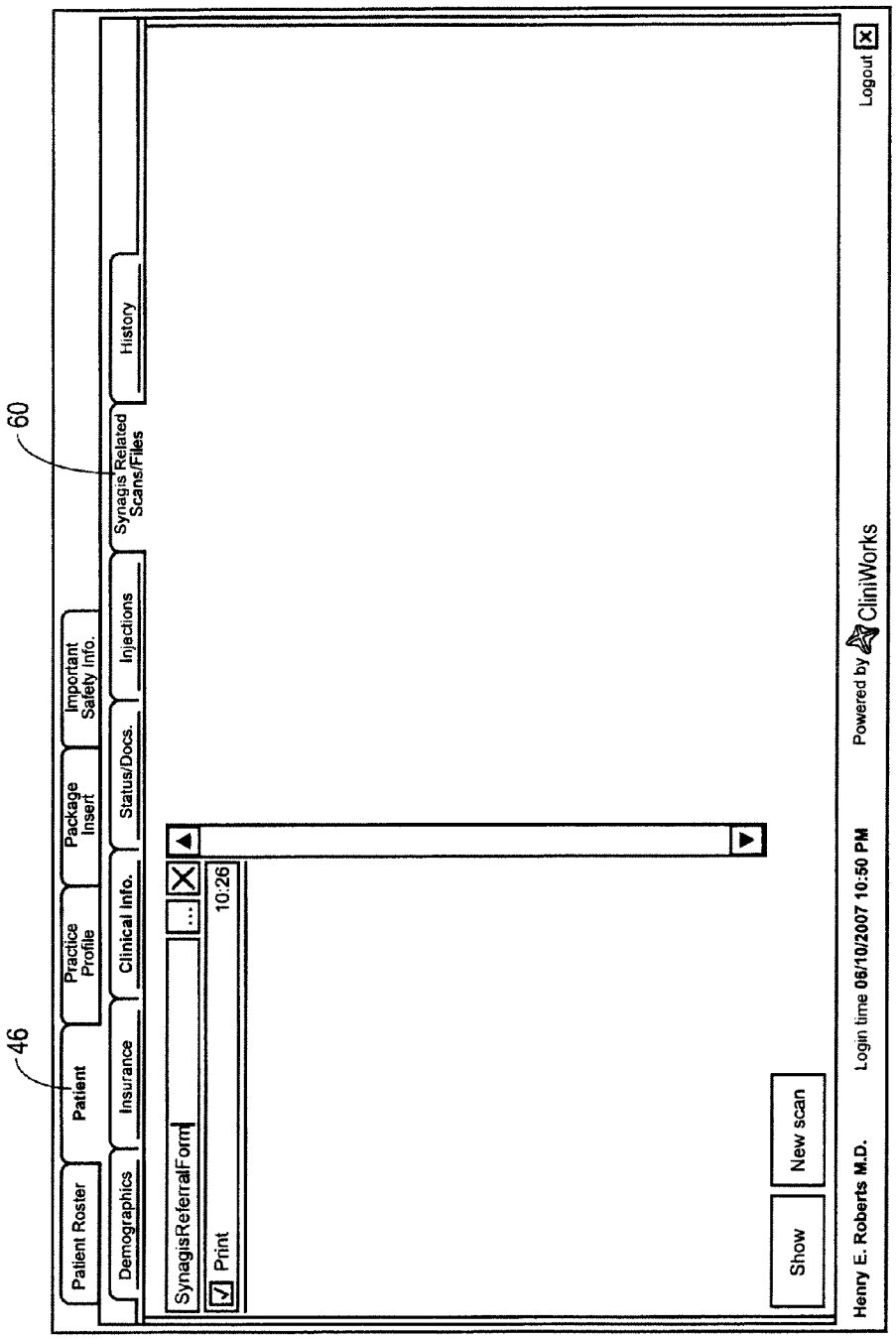
FIG. 17 illustrates an electronic form for uploading documents associated with a patient such as a NICU discharge summary in accordance with an embodiment of the present invention.
Figure 18:
FIG. 18 illustrates an electronic form for reviewing a patient specialty pharmaceutical transaction history in accordance with an embodiment of the present invention.

Referring to FIG. 17, the practitioner can use tab 60 to attach any documents 5060 relevant to a patient. Once scanned, such documents can then be associated with the record 46 for the patient that is kept in patient data store 44. A practitioner can scan in any document relevant to the patient including, but not limited to the neonatal intensive care unit history described above, scans of insurance cards, and any other documents that may be appropriate for a specialty pharmaceutical request such as a request for SYNAGIS®. Referring to FIG. 18, pharmaceutical online tracking module 43 provides a complete history of all the transactions associated with each of a given practitioner's patients. Such information can be stored in fields 58 in the records 46 for such patients in patient data store 44. Such information includes transactions involving any of the previously identified forms, including completion of such forms, scanning of patient-related documents, filling of a prescription, preparation of an appeal when a denial occurs, and so forth.

Figure 19:
FIG. 19 illustrates an electronic form for entering information about a medical practice that oversees the prescribing and administration of specialty pharmaceuticals to patients in accordance with an embodiment of the present invention.
Figure 20:
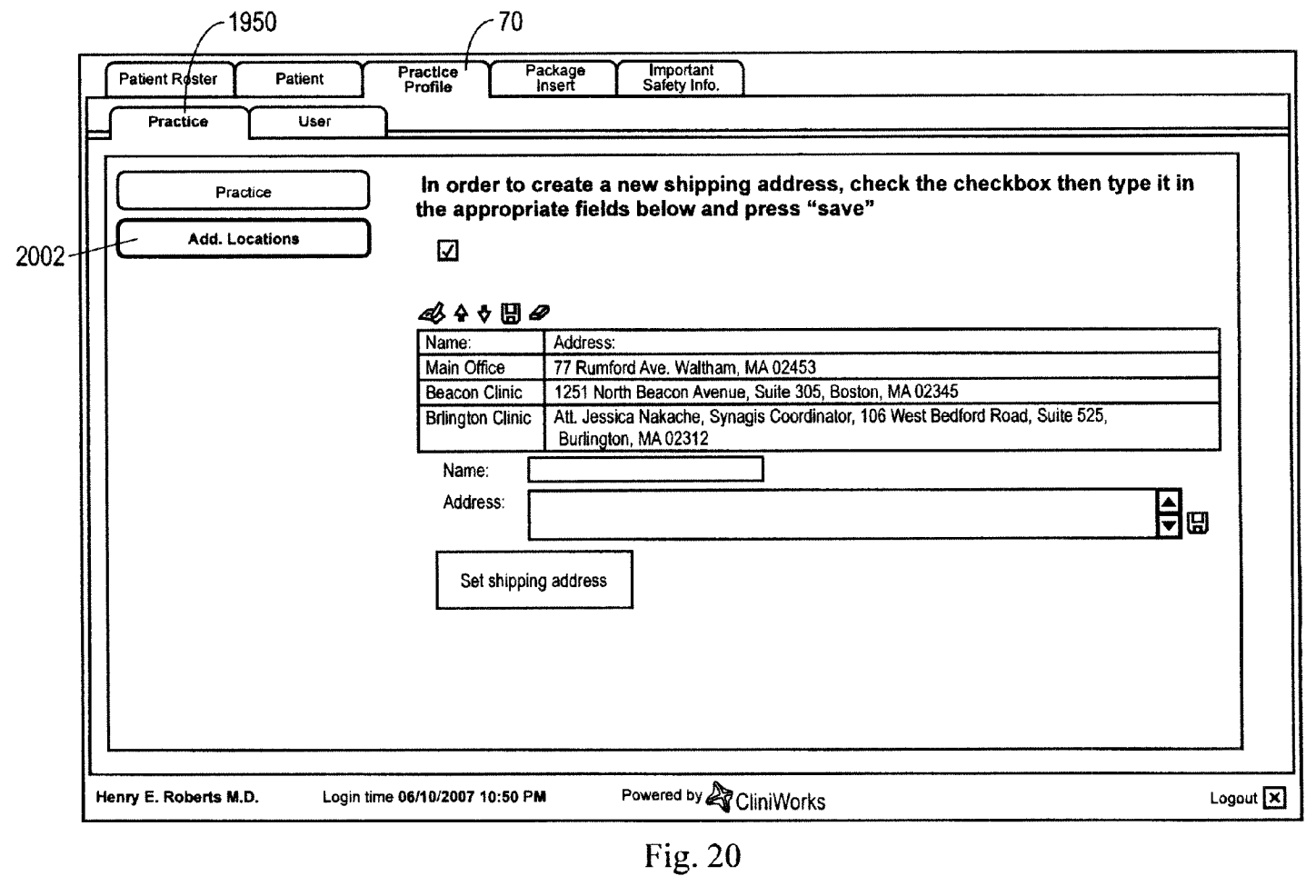

Referring to FIGS. 19 and 20, the practice profile module 70 allows a practitioner to maintain information about their practice when the practice tab 1950 is selected. For example, by selecting tab 1902 (FIG. 19) of practice module 70, the practice name, address, phone number, FAX number and office contact can be entered, stored, and retrieved. By selecting tab 2002 (FIG. 20) of practice profile module 20, additional locations and shipping addresses can be added to the practice group. For instance, consider the case where an employee at a practioner's group is assigned to be the SYNAGIS® coordinator. Further, consider that a practice can have one or more doctors and one or more locations. The employee can use the practice profile module 70 to set up all of the offices that belong in the practice, all of the doctors in the practice, the names of all the other SYNAGIS® coordinators in the practice, and so forth. Thus, the SYNAGIS® coordinator can use practice profile module 70 to do maintenance activities. In a hypothetical example, consider the practice group Fountainhead Pediatrics, in which there are between 15 and 20 doctors. Foutainhead Pediatrics has two locations. It could be the case that some of those doctors practice in both locations, so for various patients there may be a need to have the SYNAGIS® sent to location one versus location two. Practice profile module 70 can be used to manage the practice so that the SYNAGIS® is sent to the correction location.

Figure 21:
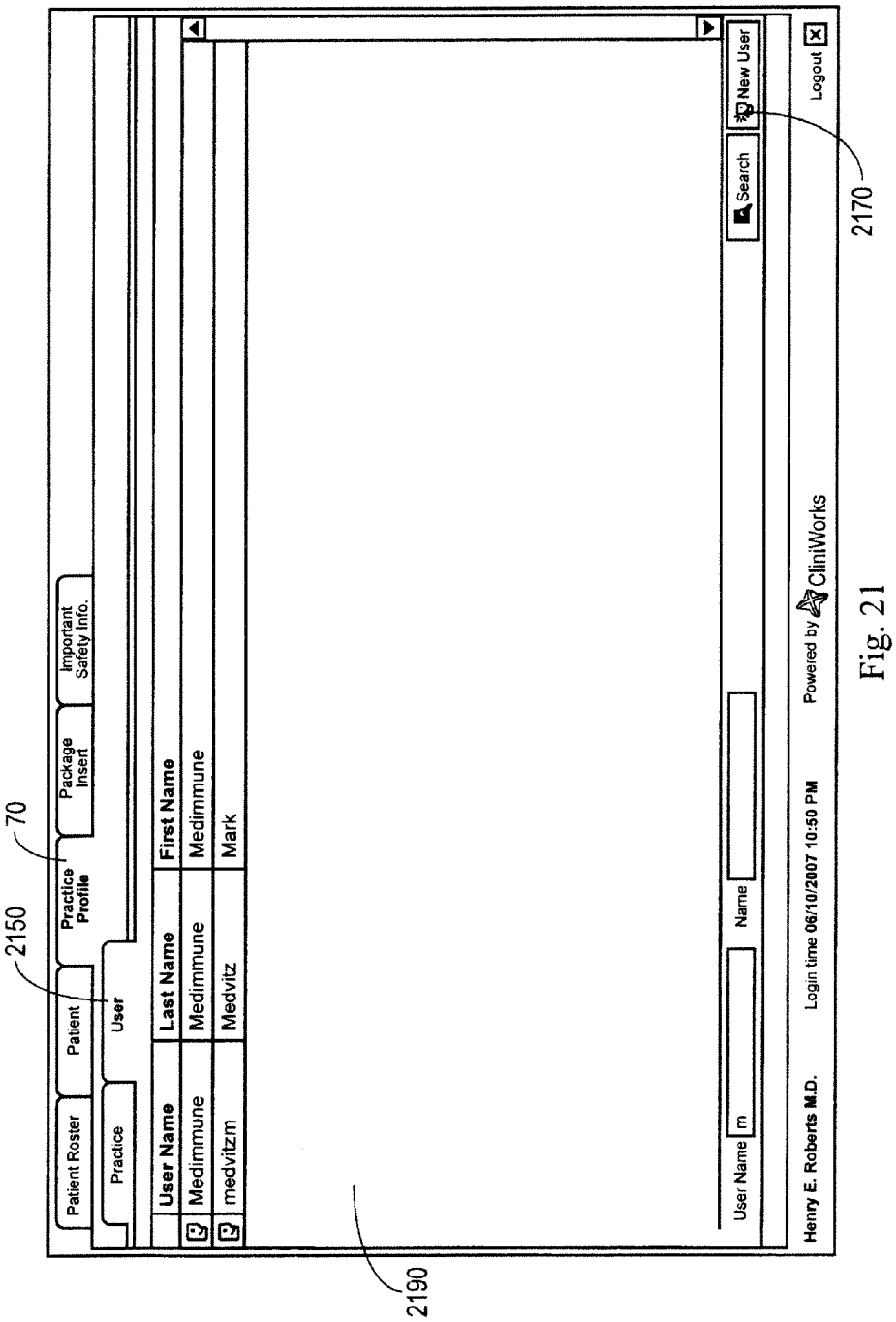
FIG. 21 illustrates a faun for specifying the medical care givers at a medical practice that oversees the prescribing and administration of specialty pharmaceuticals to patients in accordance with an embodiment of the present invention.
Figure 22:
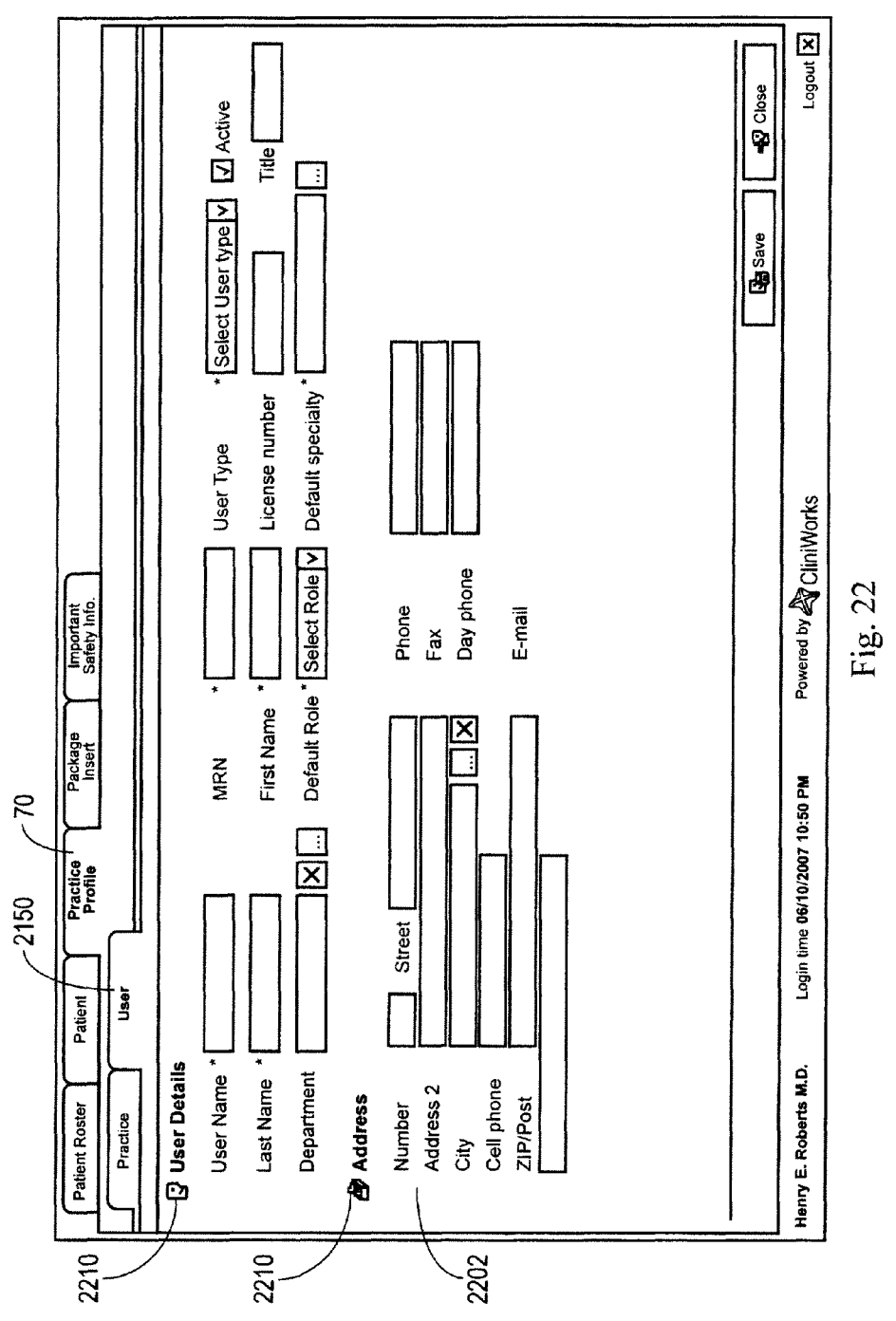

Referring to FIGS. 21 through 23, the practice profile module 70 allows a practitioner to maintain information about the account users of their practice when the practice tab 2150 is selected. For example, in FIG. 21, the full name and user name of each user of pharmaceutical online tracking module 43 in the practice group is provided. By selecting "new user" tab 2170 or any of the full names listed in panel 2190 of FIG. 21, panel 2202 illustrated in FIG. 22 is generated, where more detailed information for a user of the pharmaceutical online tracking module 43 in the practice group can be reviewed, revised, and entered. As illustrated in panel 2202 of FIG. 22, information that can be provided for each such user includes, but is not limited to, department, default role, default specialty, address, cell phone number, home phone number, FAX number, daytime phone number, and E-mail address. Panel 2202 includes toggles 2210 that allow the user to expand and collapse categories of data such as (i) user details, (ii) address, (iii) associations, and (iv) an eForm. For example, referring to FIG. 23, Address, Associations, and eForm have all been collapsed leaving only user details.

Figure 24:
FIG. 24 illustrates an electronic mechanism for providing package insert information for a specialty pharmaceutical that is supported by a pharmaceutical online tracking module in accordance with an embodiment of the present invention.
Figure 25:
FIG. 25 illustrates an electronic mechanism for providing safety information for a specialty pharmaceutical that is supported by a pharmaceutical online tracking module in accordance with an embodiment of the present invention.

Referring to FIG. 24, package insert 72 provides the complete package insert of any specialty pharmaceutical supported by pharmaceutical online tracking module 43, including but not limited to SYNAGIS®. Package insert 72 provides a detailed description of the composition of each specialty pharmaceutical supported by pharmaceutical online tracking module 43. Referring to FIG. 25, safety information 74 is provided. Safety information 74 indicates what diseases and symptoms each specialty pharmaceutical supported by pharmaceutical online tracking module 43 can be used to treat.

In some embodiments, pharmaceutical online tracking module 43 further provides the ability to generate a schedule for when a patient should receive the specialty pharmaceutical. This schedule can be stored in the patient record 46 associated with the patient. Furthermore, in some embodiments, pharmaceutical online tracking module 43 can send an alert to a care practitioner or patient at a time prior to when the patient is due for a dosage of the predetermined pharmaceutical (e.g., the hour before, the day before, the week before, etc.) as determined by the calendar. In some embodiments, pharmaceutical online tracking module 43 further provides a calendar so that when a practitioner logs onto module 43, a calendar is presented that provide all upcoming activity associated the patients in the practitioner's office that receive a particular specialty drug (e.g., SYNAGIS®). In some embodiments, pharmaceutical online tracking module 43 sends a message to a specialty pharmacy distributor a couple of weeks ahead of time before a dosage is due for a patient, to ensure that the distributor ships the drug to the practitioner's office in time for the scheduled administration.

In some embodiments, specialty pharmacy distributors are able to link back to pharmaceutical online tracking module 43 so that, rather than requiring the practitioner's office to proactively track the status or disposition of a prescription request, the specialty pharmacy distributor can perform the task by processing the prescription and uploading the status of the approval process into pharmaceutical online tracking module 43 (e.g., whether the prescription has been denied, is under review, been received, or been approved).

Typically the type of clinical criteria for approving a given specialty pharmaceutical varies from insurer to insurer. The default mode for pharmaceutical online tracking module 43 is to obtain and store sufficient clinical information for a given patient so that there is enough information to satisfy the queries of any supported insurer for a given specialty pharmaceutical, regardless of what particular clinical the supported insurer may demand in order approve the given specialty pharmaceutical. In some alternative embodiments, however, the clinical information that is queried for and stored for a given patient is determined by the identity of the patient's insurer. In this way, rather than requesting a large set of clinical information, only the subset of clinical information that is required of a given patient's insurer is stored for the patient. This is advantageous because it reduces the amount of information that the clinical practitioner has to input into the record 46 stored for the patient.

In some embodiments each medical practitioner logs into pharmaceutical online tracking module 43 and maintains an account with the module. Further, each respective medical practitioner or respective medical practitioner group only has access to the patient records 46 of the patients of the respective medical practitioner or respective medical practitioner group. Advantageously, as illustrated in FIG. 26, when a practitioner in a medical group logs into pharmaceutical online tracking module 43, the practitioner can review a patient roster which includes the names of all the patients that receive care at the medical group. The roster can include information such as referral number, patient name, location where care is given, the name of the responsible doctor within the practice group, the name of the patient's insurer, the name of the patient's specialty pharmaceutical delivery (SPD) service and the status time. As further illustrated in FIG. 26, the patient roster can be queried based on any combination of date, status, provider, location, first name, and last name.

In some embodiments, each specialty pharmacists logs into pharmaceutical online tracking module 43 and maintains an account with the module. Further, each respective specialty pharmacists only has access to the patient records 46 of the patients of the respective specialty pharmacists. In some embodiments, insurers, including prescription benefit managers, that cover specialty pharmaceuticals do not have access to pharmaceutical online tracking module 43 but, rather, receive all their information from specialty pharmacists. In some embodiments each insurer does have access to pharmaceutical online tracking module 43. In some embodiments each insurer logs into pharmaceutical online tracking module 43 and maintains an account with the module. Further, each respective insurer only has access to the patient records 46 of the patients of the respective medical practitioner or respective medical practitioner group. In typical embodiments, the manufacturers of the specialty pharmaceuticals tracked by pharmaceutical online tracking module 43 do not have access to patent records 46. In some embodiments, manufacturers of the specialty pharmaceuticals tracked by pharmaceutical online tracking module 43 only have Health Insurance Portability and Accountability Act (HIPAA) compliant access to patient data store 44 and, in particular, patient records 46.

Computer and Computer Program Product Implementations

The present invention can be implemented as a tangible computer program product that comprises a computer program mechanism embedded in a tangible computer-readable storage medium. Further, any of the methods of the present invention can be implemented in one or more computers. Further still, any of the methods of the present invention can be implemented in one or more computer program products. Some embodiments of the present invention provide a computer program product that encodes any or all of the methods disclosed herein. Such methods can be stored on a CD-ROM, DVD, magnetic disk storage product, or any other computer-readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise.

Some embodiments of the present invention provide a computer program product that contains any or all of the program modules shown in FIG. 1 and/or any or all of the methods disclosed herein. These program modules can be stored on a CD-ROM, DVD, magnetic disk storage product, or any other tangible computer-readable data or tangible program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices.

Clinical Information

Examples of clinical information have been provided above in conjunction with the input to FIG. 6 through 10. Additional examples of clinical information include, but are not limited to the examples provided in this section. In some embodiments, clinical information is abundance data of mRNA transcripts, cDNAs, or cRNAs for mRNA transcribed from the gene, or nucleic acid derived from any of the foregoing that are measured from a biological sample from the patient. Furthermore, in some embodiments, clinical information is abundance data of proteins or fragments thereof that are measured from a biological sample from the patient. Additional examples of clinical information include, but are not limited to, response to treatment, e.g. administration of a drug, efficacy of a drug, predisposition to a disease, a stage of a disease, efficacy of a drug as a function of drug dosage, bone density, cholesterol level, obesity, blood sugar level, eye color, blood type, coordination, percentage body fat (PBF), waist-to-hip ratio (WHR), fasting serum concentrations of triglycerides (TAG), fasting serum concentrations of total cholesterol (CHOL), and fasting serum concentrations of glucose (GLUC).

In some embodiments, clinical information comprises observations made by a patient's physician. In some instances, the observations made by a physician include, or can be represented by, a code from the International Classification of Diseases, $9^{th}$ Revision, prepared by the Department of Health and Human Services (ICD-9 codes), or an equivalent. The clinical information can include laboratory test results (e.g., cholesterol level, high density lipoprotein/low density lipoprotein ratios, triglyceride levels, etc.), statements made by the patient about their health, x-rays, biopsy results, and any other medical info nation typically relied upon by a doctor to make a diagnosis of the patient.

References Cited

All references cited herein are incorporated herein by reference in their entirety and for all purposes to the same extent as if each individual publication or patent or patent application was specifically and individually indicated to be incorporated by reference in its entirety herein for all purposes.

Modifications

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed:

1. A method for processing a request for a prescription for the specialty pharmaceutical palivizumab using software dedicated to processing requests for prescriptions solely for palivizumab, the method comprising:
  (A) obtaining with a user interface device of a provider system prescription information for palivizumab for a patient, the user interface device comprising a user input device and a display device, the software causing the display device to display an electronic form dedicated to receiving the prescription information solely for palivizumab, wherein the prescription information comprises a plurality of elements, the electronic form comprising blocks for receiving via the user input device elements comprising (i) information identifying the patient, and (ii) a prescription for an amount of palivizumab;
  (B) receiving with the user interface device patient clinical information, the software causing the display device to display an electronic form dedicated to receiving patient clinical information relevant to palivizumab, wherein the patient clinical information comprises a plurality of determinants which collectively assist in determining whether a patient is a good candidate for palivizumab and contribute to a basis for authorizing or denying coverage to said patient for palivizumab, the electronic form comprising at least five blocks for receiving via the user input device a corresponding at least five determinants from the group of determinants consisting of
    a gestational age of the patient,
    a weight of the patient,
    a categorical indication as to whether the patient has congenital heart disease,
    a categorical indication as to whether the patient has chronic respiratory disease arising in the perinatal period,
    a categorical indication as to whether the patient has a chronic pulmonary disease,
    a categorical indication as to whether the patient has a congenital anomaly of the respiratory system, and
    for at least one of said categorical indications, one or more additional determinants associated with the categorical indication;
  wherein at least one determinant is not a standardized code;
  (C) storing the prescription information and the patient clinical information in a non-transitory computer-readable medium;
  (D) requesting coverage for the patient for palivizumab by sending the prescription information and the patient clinical information from the provider system to a specialty pharmacy that is configured to use the prescription information and the patient clinical information to make a coverage decision as to whether to grant coverage to said patient for palivizumab, wherein said coverage decision made by the pharmacy is based upon (i) a set of guidelines provided by an insurer of the patient, (ii) the prescription information, and (iii) the patient clinical information; and
  (E) displaying with the display device the coverage decision made by the pharmacy.

2. The method of claim 1, wherein the electronic form dedicated to receiving patient clinical information relevant to palivizumab further comprises one or more blocks for receiving via the user input device at least one determinant comprising an indication of whether the patient spent time in a neonatal intensive care unit (NICU).

3. The method of claim 1, wherein the electronic form dedicated to receiving patient clinical information relevant to palivizumab comprises one or more blocks for receiving via the user input device at least one determinant associated with congenital heart disease, said associated determinant selected from the group of determinants consisting of
(i) a categorical indication as to whether the patient has a moderate pulmonary hypertension or a severe pulmonary hypertension,
(ii) an identity of a medication that is being given to the patient for the congenital heart disease, and
(iii) a date when the medication for the congenital heart disease was administered to the patient.

4. The method of claim 1, wherein the electronic form dedicated to receiving patient clinical information relevant to palivizumab comprises one or more blocks for receiving via the user input device at least one determinant associated with chronic pulmonary disease, said associated determinant selected from the group of determinants consisting of
(i) a categorical indication as to whether the patient receives supplemental oxygen,
(ii) a categorical indication as to whether the patient receives a corticosteroid,
(iii) a categorical indication as to whether the patient receives a diuretic, and
(iv) a categorical indication as to whether the patient receives a bronchodilator.

5. The method of claim 1, wherein said coverage decision comprises determining an age of the patient from the patient clinical information or the prescription information and wherein coverage to said patient for palivizumab is denied when the patient is more than two years old.

6. The method of claim 1, wherein the electronic form dedicated to receiving patient clinical information relevant to palivizumab comprises one or more blocks for receiving via the user input device one or more risk factors selected from the group consisting of
a categorical indication as to whether the patient has a school-age sibling,
a categorical indication as to whether the patient has been subjected to an air pollutant,
a categorical indication as to whether the patient attends day care,
a categorical indication as to whether the patient has severe neuromuscular disease,
a categorical indication as to whether the patient is subject to crowded living conditions,
a categorical indication as to whether the patient had a birth weight of less than 2500 grams,
a categorical indication as to whether the patient was part of a multiple birth,
a categorical indication as to whether there is a history of asthma in the patient's family,
a categorical indication as to whether the patient suffers from a congenital abnormality or airway, and
a categorical indication as to whether the patient has been exposed to tobacco smoke.

7. The method of claim 1, wherein the electronic form dedicated to receiving patient clinical information relevant to palivizumab comprises five or more blocks for receiving via the user input device a corresponding five or more risk factors selected from the group consisting of
a categorical indication as to whether the patient has a school-age sibling,
a categorical indication as to whether the patient has been subjected to an air pollutant,
a categorical indication as to whether the patient attends day care,
a categorical indication as to whether the patient has severe neuromuscular disease,
a categorical indication as to whether the patient is subject to crowded living conditions,
a categorical indication as to whether the patient had a birth weight of less than 2500 grams,
a categorical indication as to whether the patient was part of a multiple birth,
a categorical indication as to whether there is a history of asthma in the patient's family,
a categorical indication as to whether the patient suffers from a congenital abnormality or airway, and
a categorical indication as to whether the patient has been exposed to tobacco smoke.

8. The method of claim 1, wherein the requesting (D) comprises sending the prescription information and the patient clinical information from the provider system to a remote computer associated with the pharmacy in a packet-based form over a wide area network or Internet.

9. The method of claim 8, wherein the prescription information and the clinical information is sent in a secure manner over the wide area network or Internet.

10. The method of claim 8, wherein the prescription information and the patient clinical information is sent using the Hypertext Transport Protocol over a secure socket layer.

11. The method of claim 1, wherein the requesting (D) comprises sending the prescription information and the patient clinical information to the pharmacy by FAX or email.

12. The method of claim 1, wherein the electronic form dedicated to receiving prescription information for palivizumab for the patient further includes one or more blocks for receiving via the user input device one or more insurance information elements selected from the group consisting of
an identification of the primary insurer for the patient,
a primary cardholder name,
a primary cardholder social security number,
a primary policy number,
a primary insurer telephone number,
a primary employer,
a primary group number,
an identification of a secondary insurer for the patient,
a secondary cardholder name,
a secondary cardholder social security number,
a secondary policy number,
a secondary insurer telephone number, a secondary employer, and
a secondary group number.

13. The method of claim 1, wherein the electronic form dedicated to receiving prescription information for palivizumab for the patient further includes six or more blocks for receiving via the user input device a corresponding six or more insurance information elements selected from the group consisting of
an identification of the primary insurer for the patient,
a primary cardholder name,
a primary cardholder social security number,
a primary policy number,
a primary insurer telephone number,
a primary employer,
a primary group number,
an identification of a secondary insurer for the patient,
a secondary cardholder name,
a secondary cardholder social security number, a secondary policy number,
a secondary insurer telephone number,
a secondary employer, and
a secondary group number.

14. The method of claim 1, wherein the requesting (D) is done without human intervention.

15. The method of claim 1, wherein each determinant is not a standardized code.

16. The method of claim 1, wherein the electronic form dedicated to receiving prescription information for palivizumab for the patient further includes a plurality of blocks for receiving via the user input device elements comprising
    (i) at least one element comprising palivizumab delivery instructions selected from the group of an indication as to whether delivery to be made to the patient's home or to a medical facility, name of agency providing a home visit, name of medical facility, and delivery address; and
    (ii) at least one element comprising palivizumab administration information selected from the group of an amount of palivizumab to be administered to the patient, whether epinephrine is to be administered to the patient, known allergies of the patient, one or more scheduled dates for administration of palivizumab, number of doses of palivizumab to be administered, and dates of completed administrations.

17. The method of claim 1, wherein the plurality of determinants collectively satisfies the requirements of a plurality of supported insurers for palivizumab.

18. The method of claim 1, wherein the combination of supplying patient clinical information together with a prescription request is outside of a standards-based e-prescribing system.

19. A non-transitory computer-readable medium storing a computer program product, executable by a computer comprising a user interface device having a user input device and a display device, to process a request for a prescription solely for the specialty pharmaceutical palivizumab, the computer program product comprising instructions for causing the computer to perform the steps of:
    (A) obtaining with the user interface device prescription information for palivizumab for a patient, the instructions causing the display device to display an electronic form dedicated to receiving the prescription information solely for palivizumab, wherein the prescription information comprises a plurality of elements, the electronic form comprising blocks for receiving via the user input device elements comprising (i) information identifying the patient, and (ii) a prescription for an amount of palivizumab;
    (B) receiving with the user interface device patient clinical information, the instructions causing the display device to display an electronic form dedicated to receiving the patient clinical information relevant to palivizumab, wherein the patient clinical information comprises a plurality of determinants which collectively assist in determining whether a patient is a good candidate for palivizumab and contribute to a basis for authorizing or denying coverage to said patient for palivizumab, the electronic form comprising at least five blocks for receiving via the user input device a corresponding at least five determinants from the group of determinants consisting of
    a gestational age of the patient,
    a weight of the patient,
    a categorical indication as to whether the patient has congenital heart disease,
    a categorical indication as to whether the patient has chronic respiratory disease arising in the perinatal period,
    a categorical indication as to whether the patient has a chronic pulmonary disease,
    a categorical indication as to whether the patient has a congenital anomaly of the respiratory system, and
    for at least one of said categorical indications, one or more additional determinants associated with the categorical indication;
    wherein at least one determinant is not a standardized code;
    (C) storing the prescription information and the patient clinical information in a non-transitory computer-readable medium;
    (D) requesting approval for the patient for palivizumab by sending the prescription information and the patient clinical information from the computer to a specialty pharmacy that is configured to use the prescription information and the patient clinical information to make a coverage decision as to whether to grant coverage to said patient for palivizumab, wherein said coverage decision made by the pharmacy is based upon (i) a set of guidelines provided by an insurer of the patient, (ii) the prescription information, and (iii) the patient clinical information; and
    (E) displaying with the display device the coverage decision made by the pharmacy.

20. An apparatus for processing a request for a prescription for the specialty pharmaceutical palivizumab that requires preauthorization based upon clinical data of a patient, the apparatus comprising:
    a user interface device comprising a user input device and a display device;
    a processor coupled to the user interface device; and
    a memory, coupled to the processor, the memory storing a module comprising instructions for causing the processor to perform the steps of:
    (A) obtaining with the user interface device prescription information for palivizumab for a patient, the instructions causing the display device to display an electronic form dedicated to receiving the prescription information solely for palivizumab, wherein the prescription information comprises a plurality of elements, the electronic form comprising blocks for receiving via the user input device elements comprising (i) information identifying the patient and (ii) a prescription for an amount of palivizumab;
    (B) receiving with the user interface device patient clinical information, the instructions causing the display device to display an electronic form dedicated to receiving the patient clinical information relevant to palivizumab wherein the patient clinical information comprises a plurality of determinants which collectively assist in determining whether a patient is a good candidate for palivizumab and contribute to a basis for authorizing or denying coverage to said patient for palivizumab, the electronic form comprising at least five blocks for receiving via the user input device a corresponding at least five determinants from the group of determinants consisting of
    a gestational age of the patient,
    a weight of the patient,
    a categorical indication as to whether the patient has congenital heart disease,
    a categorical indication as to whether the patient has chronic respiratory disease arising in the perinatal period, a categorical indication as to whether the patient has a chronic pulmonary disease, a categorical indication as to whether the patient has a congenital anomaly of the respiratory system, and for at least one of said categorical indications, one or more additional determinants associated with the categorical indication;

wherein at least one determinant is not a standardized code;

(C) storing the prescription information and the patient clinical information in a non-transitory computer-readable medium;

(D) requesting approval for the patient for palivizumab by sending the prescription information and the patient clinical information from the apparatus to a specialty pharmacy that is configured to use the prescription information and the patient clinical information to make a coverage decision as to whether to grant coverage to said patient for palivizumab, wherein said coverage decision made by the pharmacy is based upon (i) a set of guidelines provided by an insurer of the patient, (ii) the prescription information, and (iii) the patient clinical information; and (E) displaying with the display device the coverage decision made by the pharmacy.

* * * * *